United States Patent
Nagai et al.

(10) Patent No.: US 11,084,792 B2
(45) Date of Patent: Aug. 10, 2021

(54) METHOD FOR PRODUCING DIFLUOROMETHYLENE COMPOUND

(71) Applicant: SATO PHARMACEUTICAL CO., LTD., Tokyo (JP)

(72) Inventors: Keita Nagai, Matsudo (JP); Toshihiko Ozaki, Imizu (JP)

(73) Assignee: SATO PHARMACEUTICAL CO., LTD., Tokyo (JP)

( * ) Notice: Subject to any disclaimer, the term of this patent is extended or adjusted under 35 U.S.C. 154(b) by 130 days.

(21) Appl. No.: 16/608,802

(22) PCT Filed: Apr. 27, 2018

(86) PCT No.: PCT/JP2018/017174
§ 371 (c)(1),
(2) Date: Oct. 25, 2019

(87) PCT Pub. No.: WO2018/199284
PCT Pub. Date: Nov. 1, 2018

(65) Prior Publication Data
US 2020/0190038 A1 Jun. 18, 2020

(30) Foreign Application Priority Data
Apr. 28, 2017 (JP) .............................. JP2017-089928

(51) Int. Cl.
*C07D 231/56* (2006.01)

(52) U.S. Cl.
CPC ................................. *C07D 231/56* (2013.01)

(58) Field of Classification Search
CPC .................................................. C07D 231/56
See application file for complete search history.

(56) References Cited

U.S. PATENT DOCUMENTS

| 9,512,119 B2 * | 12/2016 | Nagai ................... C07D 209/08 |
| 2014/0005221 A1 | 1/2014 | Nagai et al. |
| 2015/0191463 A1 | 7/2015 | Nagai et al. |
| 2015/0203490 A1 | 7/2015 | Nagai et al. |
| 2017/0044158 A1 | 2/2017 | Nagai et al. |

FOREIGN PATENT DOCUMENTS

| EP | 2 669 270 A1 | 12/2013 |
| EP | 2 878 594 A1 | 6/2015 |
| WO | 2014/017643 A1 | 1/2014 |

OTHER PUBLICATIONS

International Preliminary Report on Patentability and Written Opinion issued in PCT/JP2018/017174; dated Oct. 29, 2019.
International Search Report issued in PCT/JP2018/017174; dated Jul. 24, 2018.
Boulouard et al.; "4-Substituted indazoles as new inhibitors of neuronal nitric oxide synthase"; Bioorganic & Medicinal Chemistry Letters; May 10, 2007; pp. 3177-3180; vol. 17; No. 11; Pergamon Amsterdam, NL.
The extended European search report issued by the European Patent Office dated Jul. 24, 2020, which corresponds to European Patent Application No. 18791983.2-1110 and is related to U.S. Appl. No. 16/608,802.

\* cited by examiner

*Primary Examiner* — Rebecca L Anderson
(74) *Attorney, Agent, or Firm* — Studebaker & Brackett PC

(57) ABSTRACT

The present invention provides a method for producing a difluoromethylene compound and an intermediate thereof, which are useful in the field of pharmaceuticals.
Specifically provided is a method for producing a difluoromethylene compound, including a step of allowing a compound represented by formula (6):

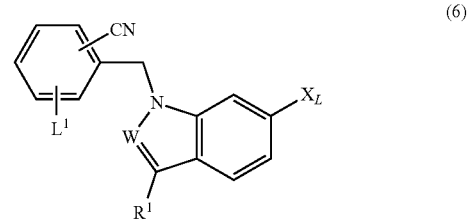

(6)

[wherein $L^1$ represents a halogen atom, a cyano group, a lower alkyl group, a halo-lower alkyl group, a cycloalkyl group, a lower alkoxy group, a halo-lower alkoxy group, or a hydroxy lower alkyl group; $R^1$ represents a lower alkyl group, a halogen atom, a halo-lower alkyl group, a cycloalkyl group, a cyano group, or a hydroxy lower alkyl group; and W represents a nitrogen atom or a methine group] to react with a compound represented by formula (7):

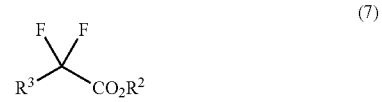

(7)

[wherein $R^2$ represents a lower alkyl group, a halo-lower alkyl group, a cycloalkyl group, a lower alkenyl group, or an aralkyl group; and $R^3$ represents a chlorine atom, a bromine atom, or an iodine atom].

16 Claims, No Drawings

METHOD FOR PRODUCING DIFLUOROMETHYLENE COMPOUND

TECHNICAL FIELD

The present invention relates to a novel method for producing a difluoromethylene compound and an intermediate thereof, which are useful in the field of pharmaceuticals. More specifically, the present invention relates to a novel method for producing a difluoromethylene compound and an intermediate thereof, which have a URAT1 inhibitory activity and are useful in the field of treatment for diseases associated with blood uric acid. In addition, the present invention also relates a novel compound for producing a difluoromethylene compound and an intermediate thereof, which are useful in the field of pharmaceuticals.

BACKGROUND ART

A compound having a URAT1 inhibitory activity is believed to reduce the blood uric acid level, by suppressing the re-absorption of uric acid in the proximal convoluted tubule and increasing the excretion of uric acid, and is useful as an agent for treating or preventing a pathological condition associated with uric acid, specifically, hyperuricemia, gouty node, gouty arthritis, gouty kidney, urolithiasis, and renal function disorder. In addition, the compound is also useful as an agent for treating or preventing hypertension, hyperlipidemia, abnormal glucose tolerance, obesity, coronary artery disease, and cerebrovascular disorders, which are associated with hyperuricemia.

Incidentally, Patent Literature 1 discloses that a difluoromethylene compound represented by formula (I):

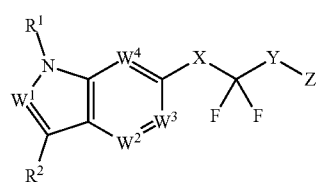

(I)

or a pharmacologically acceptable salt or ester thereof has an excellent URAT1 inhibitory activity and thus can reduce the uric acid level in the blood, and is useful as an agent for treating or preventing for symptoms associated with blood uric acid, such as hyperuricemia, gouty node, acute gouty arthritis, chronic gouty arthritis, gouty kidney, urolithiasis, renal function disorder, coronary artery diseases, or ischemic heart disease, for example.

In addition, as a general method for synthesizing a difluoromethylene compound of the above formula (I) wherein X and Y are single bonds, and Z is a carboxylic acid, Patent Literature 1 discloses (1) a method through Scheme 2, Scheme 6, Scheme 7, and the removal of a protective group, and (2) a method through Scheme 3, Scheme 4, Scheme 5, and the removal of a protective group.

CITATION LIST

Patent Literature

Patent Literature: WO 2014/017643

SUMMARY OF INVENTION

Technical Problem

However, the present inventors have found that the synthesis method of Patent Literature 1 described above has problems due to use of column chromatography, and also in terms of yield, in the industrial production of a difluoromethylene compound represented by formula (I) of Patent Literature 1, wherein X and Y are single bonds, and Z is a carboxylic acid, or a salt thereof.

Incidentally, column chromatography requires use of a large amount of organic solvent (mobile phase), concentration of fractions over time, and also use of a large amount of silica gel. Therefore, frequent use of column chromatography leads to a significant increase in the production cost. Therefore, it is preferable to avoid the use of column chromatography in industrial production.

Solution to Problem

In order to solve the problems described above, the present inventors have conducted extensive research about the method for producing a difluoromethylene compound, and consequently found a method suitable for the industrial production of a difluoromethylene compound using a starting material having a specified structure nowhere described in Patent Literature 1 (compound represented by formula (1) in the present invention) and also a step of introducing a difluoroacetic acid group nowhere described in Patent Literature 1 (step (E) in the present invention). The present invention has been made based on such findings.

That is, the present invention relates to the following [1] to [24].

[1] A method for producing a compound represented by formula (9):

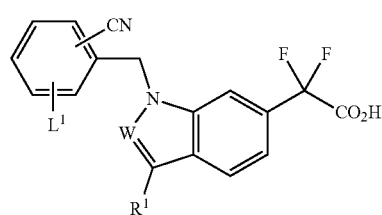

(9)

[wherein $L^1$ represents a halogen atom, a cyano group, a lower alkyl group, a halo-lower alkyl group, a cycloalkyl group, a lower alkoxy group, a halo-lower alkoxy group, or a hydroxy lower alkyl group;

$R^1$ represents a lower alkyl group, a halogen atom, a halo-lower alkyl group, a cycloalkyl group, a cyano group, or a hydroxy lower alkyl group; and W represents a nitrogen atom or a methine group], the method comprising the following steps (A) to (F):

a step (A): a step of allowing a compound represented by formula (1):

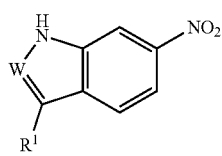
(1)

[wherein $R^1$, and W are as defined above]
to react with a compound represented by formula (2):

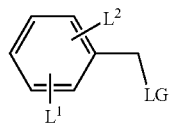
(2)

[wherein
$L^1$ is as defined above;
$L^2$ is a halogen atom or a group represented by —$OSO_2R^4$;
$R^4$ represents a lower alkyl group, a halo-lower alkyl group, or an aryl group (wherein the aryl group is optionally substituted with a halogen atom, a lower alkyl group, or a lower alkoxy group);
LG is a halogen atom or a group represented by —$OSO_2R^5$; and
$R^5$ represents a lower alkyl group, a halo-lower alkyl group, or an aryl group (wherein the aryl group is optionally substituted with a halogen atom, a lower alkyl group, or a lower alkoxy group)]
to give a compound represented by formula (3):

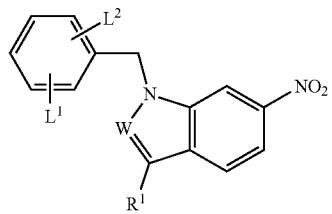
(3)

[wherein $L^1$, $L^2$, $R^1$, and W are as defined above],
a step (B): a step of cyanating $L^2$ of the compound represented by formula (3) to give a compound represented by formula (4):

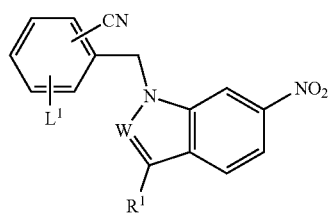
(4)

[wherein $L^1$, $R^1$, and W are as defined above],
a step (C): a step of reducing a nitro group of the compound represented by formula (4) to give a compound represented by formula (5):

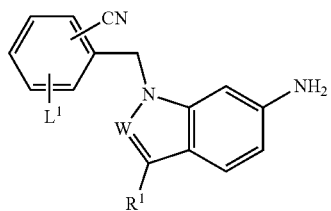
(5)

[wherein $L^1$, $R^1$, and W are as defined above]
or a salt thereof,
a step (D): a step of halogenating an amino group of the compound represented by formula (5) or salt thereof to give a compound represented by formula (6):

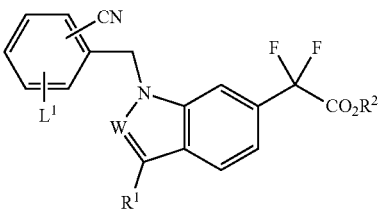
(6)

[wherein $L^1$, $R^1$, and W are as defined above, and $X_L$ is a halogen atom],
a step (E): a step of allowing the compound represented by formula (6) to react with a compound represented by formula (7):

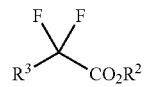
(7)

[wherein
$R^2$ represents a lower alkyl group, a halo-lower alkyl group, a cycloalkyl group, a lower alkenyl group, or an aralkyl group; and
$R^3$ represents a chlorine atom, a bromine atom, or an iodine atom]
to give a compound represented by formula (8):

(8)

[wherein $L^1$, $R^1$, $R^2$, and W are as defined above], and
a step (F): a step of removing $R^2$ of the compound represented by formula (8).

[2] A method for producing a compound represented by formula (9):

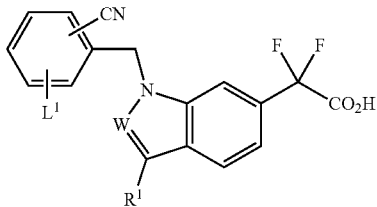

(9)

[wherein

L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group; and W represents a nitrogen atom or a methine group], the method comprising the following steps (B) to (F):

a step (B): a step of cyanating L² of a compound represented by formula (3):

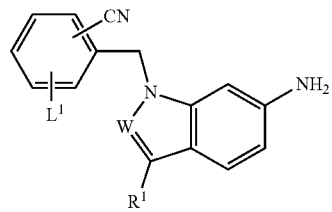

(3)

[wherein

L¹, R¹, and W are as defined above;

L² is a halogen atom or a group represented by —OSO₂R⁴; and

R⁴ represents a lower alkyl group, a halo-lower alkyl group, or an aryl group (wherein the aryl group is optionally substituted with a halogen atom, a lower alkyl group, or a lower alkoxy group)]

to give a compound represented by formula (4):

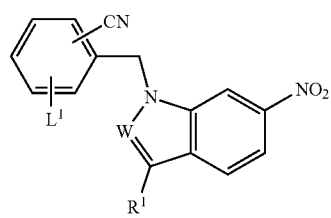

(4)

[wherein L¹, R¹, and W are as defined above], a step (C): a step of reducing a nitro group of the compound represented by formula (4) to give a compound represented by formula (5):

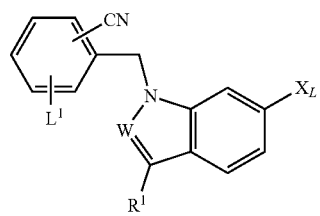

(5)

[wherein L¹, R¹, and W are as defined above]

or a salt thereof, a step (D): a step of halogenating an amino group of the compound represented by formula (5) or salt thereof to give a compound represented by formula (6):

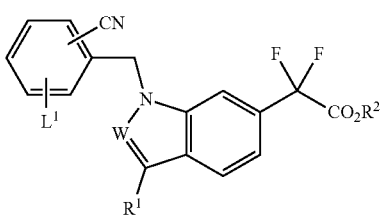

(6)

[wherein L¹, R¹, and W are as defined above, and X$_L$ is a halogen atom], a step (E): a step of allowing the compound represented by formula (6) to react with a compound represented by formula (7):

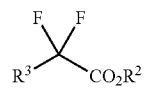

(7)

[wherein

R² represents a lower alkyl group, a halo-lower alkyl group, a cycloalkyl group, a lower alkenyl group, or an aralkyl group; and R³ represents a chlorine atom, a bromine atom, or an iodine atom]

to give a compound represented by formula (8):

(8)

[wherein L¹, R¹, R², and W are as defined above], and a step (F): a step of removing R² of the compound represented by formula (8).

[3] A method for producing a compound represented by formula (9):

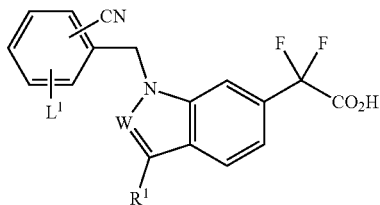

(9)

[wherein

L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group; and W represents a nitrogen atom or a methine group], the method comprising the following steps (C) to (F):

a step (C): a step of reducing a nitro group of a compound represented by formula (4):

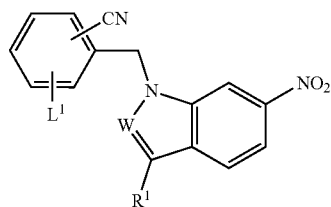

(4)

[wherein L¹, R¹, and W are as defined above]
to give a compound represented by formula (5):

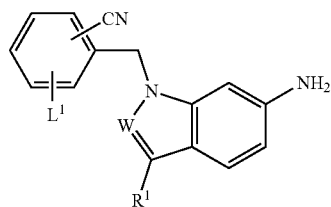

(5)

[wherein L¹, R¹, and W are as defined above]
or a salt thereof, a step (D): a step of halogenating an amino group of the compound represented by formula (5) or salt thereof to give a compound represented by formula (6):

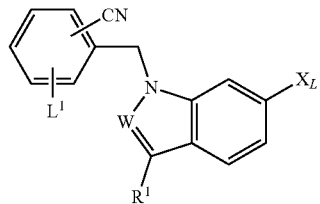

(6)

[wherein L¹, R¹, and W are as defined above, and $X_L$ is a halogen atom], a step (E): a step of allowing the compound represented by formula (6) to react with a compound represented by formula (7):

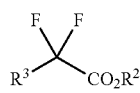

(7)

[wherein

R² represents a lower alkyl group, a halo-lower alkyl group, a cycloalkyl group, a lower alkenyl group, or an aralkyl group; and R³ represents a chlorine atom, a bromine atom, or an iodine atom]

to give a compound represented by formula (8):

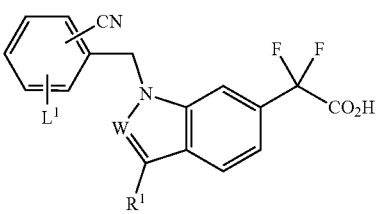

(8)

[wherein L¹, R¹, R², and W are as defined above], and a step (F): a step of removing R² of the compound represented by formula (8).

[4] A method for producing a compound represented by formula (9):

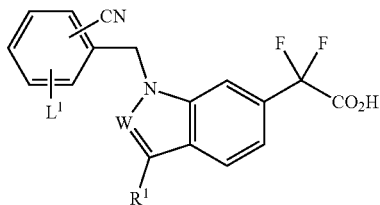

(9)

[wherein

L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group; and W represents a nitrogen atom or a methine group],
the method comprising the following steps (D) to (F):

a step (D): a step of halogenating an amino group of a compound represented by formula (5):

(5)

[wherein $L^1$, $R^1$, and W are as defined above]
or a salt thereof to give a compound represented by formula (6):

(6)

[wherein $L^1$, $R^1$, and W are as defined above, and $X_L$ is a halogen atom], a step (E): a step of allowing the compound represented by formula (6) to react with a compound represented by formula (7):

(7)

[wherein
$R^2$ represents a lower alkyl group, a halo-lower alkyl group, a cycloalkyl group, a lower alkenyl group, or an aralkyl group; and
$R^3$ represents a chlorine atom, a bromine atom, or an iodine atom]
to give a compound represented by formula (8):

(8)

[wherein $L^1$, $R^1$, $R^2$, and W are as defined above], and
a step (F): a step of removing $R^2$ of the compound represented by formula (8).

[5] A method for producing a compound represented by formula (9):

(9)

[wherein
$L^1$ represents a halogen atom, a cyano group, a lower alkyl group, a halo-lower alkyl group, a cycloalkyl group, a lower alkoxy group, a halo-lower alkoxy group, or a hydroxy lower alkyl group;
$R^1$ represents a lower alkyl group, a halogen atom, a halo-lower alkyl group, a cycloalkyl group, a cyano group, or a hydroxy lower alkyl group; and
W represents a nitrogen atom or a methine group],
the method comprising the following steps (E) to (F):
a step (E): a step of allowing a compound represented by formula (6):

(6)

[wherein
$L^1$, $R^1$, and W are as defined above; and
$X_L$ represents a halogen atom]
to react with a compound represented by formula (7):

(7)

[wherein
$R^2$ represents a lower alkyl group, a halo-lower alkyl group, a cycloalkyl group, a lower alkenyl group, or an aralkyl group; and
$R^3$ represents a chlorine atom, a bromine atom, or an iodine atom]
to give a compound represented by formula (8):

(8)

[wherein $L^1$, $R^1$, $R^2$, and W are as defined above], and
a step (F): a step of removing $R^2$ of the compound represented by formula (8).

[6] A method for producing a compound represented by formula (3):

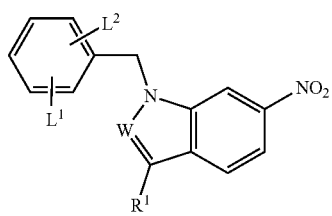
(3)

[wherein

L$^1$ represents a halogen atom, a cyano group, a lower alkyl group, a halo-lower alkyl group, a cycloalkyl group, a lower alkoxy group, a halo-lower alkoxy group, or a hydroxy lower alkyl group;

L$^2$ is a halogen atom or a group represented by —OSO$_2$R$^4$;

R$^4$ represents a lower alkyl group, a halo-lower alkyl group, or an aryl group (wherein the aryl group is optionally substituted with a halogen atom, a lower alkyl group, or a lower alkoxy group);

R$^1$ represents a lower alkyl group, a halogen atom, a halo-lower alkyl group, a cycloalkyl group, a cyano group, or a hydroxy lower alkyl group; and W represents a nitrogen atom or a methine group], the method comprising the following step (A): a step of allowing a compound represented by formula (1):

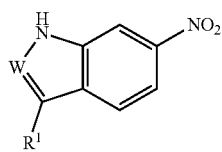
(1)

[wherein R$^1$, and W are as defined above]
to react with a compound represented by formula (2):

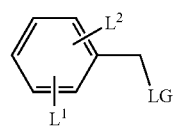
(2)

[wherein

L$^1$, L$^2$, and R$^4$ are as defined above;

LG is a halogen atom or a group represented by —OSO$_2$R$^5$; and

R$^5$ represents a lower alkyl group, a halo-lower alkyl group, or an aryl group (wherein the aryl group is optionally substituted with a halogen atom, a lower alkyl group, or a lower alkoxy group)].

[7] A method for producing a compound represented by formula (4):

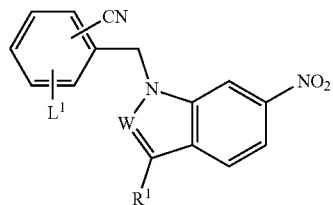
(4)

[wherein

L$^1$ represents a halogen atom, a cyano group, a lower alkyl group, a halo-lower alkyl group, a cycloalkyl group, a lower alkoxy group, a halo-lower alkoxy group, or a hydroxy lower alkyl group;

R$^1$ represents a lower alkyl group, a halogen atom, a halo-lower alkyl group, a cycloalkyl group, a cyano group, or a hydroxy lower alkyl group; and W represents a nitrogen atom or a methine group], the method comprising the following step (B): a step of cyanating L$^2$ of a compound represented by formula (3):

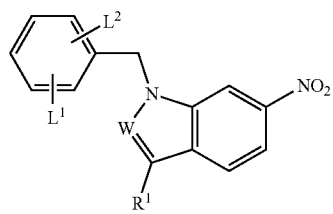
(3)

[wherein

L$^1$, R$^1$, and W are as defined above;

L$^2$ is a halogen atom or a group represented by —OSO$_2$R$^4$; and

R$^4$ represents a lower alkyl group, a halo-lower alkyl group, or an aryl group (wherein the aryl group is optionally substituted with a halogen atom, a lower alkyl group, or a lower alkoxy group)].

[8] A method for producing a compound represented by formula (5):

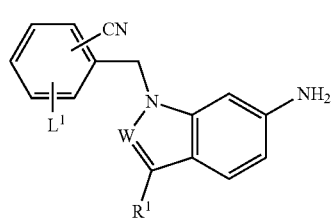
(5)

[wherein

L$^1$ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group; and W represents a nitrogen atom or a methine group], the method comprising the following step (C): a step of reducing a nitro group of a compound represented by formula (4):

(4)

[wherein L¹, R¹, and W are as defined above]
or a salt thereof.

[9] A method for producing a compound represented by formula (6):

(6)

[wherein

L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group; and W represents a nitrogen atom or a methine group], the method comprising the following step (D): a step of halogenating an amino group of a compound represented by formula (5):

(5)

[wherein L¹, R¹, and W are as defined above]
or a salt thereof.

[10] A method for producing a compound represented by formula (8):

(8)

[wherein

L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group;

R² represents a lower alkyl group, a halo-lower alkyl group, a cycloalkyl group, a lower alkenyl group, or an aralkyl group; and W represents a nitrogen atom or a methine group], the method comprising the following step (E): a step of allowing a compound represented by formula (6):

(6)

[wherein

L¹, R¹, and W are as defined above; and $X_L$ is a halogen atom]

to react with a compound represented by formula (7):

(7)

[wherein

R² is as defined above; and

R³ represents a chlorine atom, a bromine atom, or an iodine atom].

[11] The method according to any one of the above [1] to [10], wherein R¹ is a lower alkyl group.

[12] The method according to any one of the above [1] to [11], wherein L¹ is a lower alkyl group.

[13] The method according to any one of the above [1] to [12], wherein W is a nitrogen atom.

[14] The method according to the above [1] or [6], wherein a base used in the step (A) is potassium carbonate or cesium carbonate.

[15] The method according to the above [1] or [6], further including a step (A-2): a step of recrystallizing the compound represented by formula (3) using a recrystallization solvent that is a combination of tetrahydrofuran and methanol.

[16] The method according to the above [1], [2], or [7], wherein a cyanating agent used in the step (B) is zinc cyanide.

[17] The method according to the above [16], wherein in the step (B), a palladium catalyst or a combination of a palladium catalyst and a phosphine ligand is used.

[18] The method according to the above [1], [2], or [7], wherein a cyanating agent used in the step (B) is copper cyanide.

[19] The method according to the above [18], wherein in the step (B), proline is further added.

[20] The method according to any one of the above [1] to [5] and [10], wherein $R^2$ of the compound represented by formula (7) is a lower alkyl group.

[21] The method according to the above [20], wherein the compound represented by formula (7) is methyl bromodifluoroacetate or ethyl bromodifluoroacetate.

[22] The method according to any one of the above [1] to [5] and [10], wherein a reaction solvent in the step (E) is dimethyl sulfoxide or a mixed solvent of dimethyl sulfoxide and tetrahydrofuran.

[23] The method according to any one of the above [1] to [5], comprising, in the case where $R^2$ of the compound represented by formula (8) is a group other than a methyl group, a step of transesterifying the $R^2$ into a methyl group before the step (F).

[24] A compound of the following (a) to (g):
(a) 1-(2-iodo-6-methylbenzyl)-3-methyl-6-nitro-1H-indazole;
(b) 3-methyl-2-[(3-methyl-6-nitro-1H-indazol-1-yl)methyl]benzonitrile;
(c) 2-[(6-amino-3-methyl-1H-indazol-1-yl)methyl]-3-methylbenzonitrile;
(d) 2-[(6-amino-3-methyl-1H-indazol-1-yl)methyl]-3-methylbenzonitrile hydrochloride;
(e) 2-[(6-iodo-3-methyl-1H-indazol-1-yl)methyl]-3-methylbenzonitrile;
(f) Methyl [1-(2-cyano-6-methylbenzyl)-3-methyl-1H-indazol-6-yl]difluoroacetate; or
(g) Ethyl [1-(2-cyano-6-methylbenzyl)-3-methyl-1H-indazol-6-yl]difluoroacetate.

Effects of the Invention

As shown in the Examples below, the method of the present invention is applicable to the industrial production of a difluoromethylene compound.

Therefore, the present invention can provide an excellent industrial production method of a difluoromethylene compound.

DESCRIPTION OF EMBODIMENTS

Hereinafter, the meanings of terms used in the present invention will be descried, and the present invention will further be described in detail.

The term "lower alkyl group" used herein means a linear or branched alkyl group having a carbon number of from 1 to 6, and for example, a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-3-methylpropyl group, etc. are mentioned.

Examples of the "halogen atom" used herein include a fluorine atom, a chlorine atom, a bromine atom, and an iodine atom, and the like.

The term "halo-lower alkyl group" used herein means the above-mentioned "lower alkyl group" in which the substitutable optional position(s) is/are substituted by 1 or 2 or more, preferably 1 to 5 of identical or different halogen atom(s) mentioned above, and for example, a fluoromethyl group, a difluoromethyl group, a trifluoromethyl group, a 2-fluoroethyl group, a 1,2-difluoroethyl group, a 2,2,2-trifluoroethyl group, a pentafluoroethyl group, a chloromethyl group, a 2-chloroethyl group, a 1,2-dichloroethyl group, a 2,2,2-trichloroethyl group, and a bromomethyl group, and a iodomethyl group, etc. are mentioned.

The term "cycloalkyl group" used herein means a 3 to 8-membered aliphatic cyclic group, and for example, a cyclopropyl group, a cyclobutyl group, a cyclopentyl group, a cyclohexyl group, a cycloheptyl group, and a cyclooctyl group, etc. are mentioned.

The term "hydroxy lower alkyl group" used herein means the above-mentioned "lower alkyl group" in which the substitutable optional position(s) is/are substituted by 1 or 2 or more, preferably 1 or 2 of the hydroxy group(s), and for example, a hydroxymethyl group, a 1-hydroxyethyl group, a 1-hydroxypropyl group, a 2-hydroxyethyl group, a 2-hydroxypropyl group, a 2-hydroxy-1-methylethyl group, a 1-hydroxy-1-methylethyl group, a 1,2-dihydroxyethyl group, and a 3-hydroxypropyl group, etc. are mentioned.

The term "lower alkoxy group" used herein means a group in which the hydrogen atom of a hydroxyl group is substituted by the above-mentioned "lower alkyl group", and for example, a methoxy group, an ethoxy group, a propoxy group, an isopropoxy group, a butoxy group, a sec-butoxy group, a tert-butoxy group, a pentyloxy group, an isopentyloxy group, a hexyloxy group, and an isohexyloxy group, etc. are mentioned.

The term "halo-lower alkoxy group" used herein means the above-mentioned "lower alkoxy group" in which the substitutable optional position(s) is/are substituted by 1 or 2 or more, preferably 1 to 3 of identical or different halogen atom(s) mentioned above, and for example, a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, and an iodomethoxy group, etc. are mentioned.

The term "aryl group" used herein means an aryl group having an aromatic hydrocarbon ring having a carbon number of from 6 to 14, for example, a phenyl group, a naphthyl group, a biphenyl group, and an anthryl group, etc. are mentioned.

The term "lower alkenyl group" used herein means a linear or branched alkenyl group having a carbon number of from 2 to 6, and for example, a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1- propenyl group, a 3-methyl-2-butenyl group, and a 4-pentenyl group, etc. are mentioned.

The term "aralkyl group" used herein means the above-mentioned "lower alkyl group" in which the substitutable optional position(s) is/are substituted by 1 or 2 or more, preferably 1 or 2 of the above-mentioned "aryl group(s)", and for example, a benzyl group, a 1-phenylethyl group, a 2-phenylethyl group, a 1-naphthylmethyl group, and a 2-naphthylmethyl group, etc. are mentioned.

The term "substitutable optional position(s)" used herein means site(s) that is/are substitutable hydrogen atom(s) on a carbon atom, a nitrogen atom, an oxygen atom, and/or a sulfur atom, where the substitution of the hydrogen atom(s) is/are chemically accepted, and consequently a stable compound is obtained.

In order to specifically disclose the present invention, the respective symbols used in the formula (1) to formula (9) will further be described in detail with referring to their preferable specific examples.

$R^1$ is a lower alkyl group, a halogen atom, a halo-lower alkyl group, a cycloalkyl group, a cyano group, or a hydroxy lower alkyl group.

As the lower alkyl group for $R^1$, for example,
a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-3-methylpropyl group, etc. are mentioned, and
a methyl group, an ethyl group, a propyl group, and an isopropyl group, etc. are preferable, and
a methyl group is more preferable.

As the halogen atom for $R^1$, for example, a fluorine atom, a chlorine atom, a bromine atom, and an iodine atom, etc. are mentioned, and a chlorine atom is preferable.

As the halo-lower alkyl group for $R^1$, for example,
a fluoromethyl group, a difluoromethyl group, a trifluoromethyl group, a 2-fluoroethyl group, a 1,2-difluoroethyl group, a 2,2,2-trifluoroethyl group, a pentafluoroethyl group, a chloromethyl group, a 2-chloroethyl group, a 1,2-dichloroethyl group, a 2,2,2-trichloroethyl group, a bromomethyl group, and an iodomethyl group, etc. are mentioned, and
a difluoromethyl group and a trifluoromethyl group are preferable, and
a trifluoromethyl group is more preferable.

As the cycloalkyl group for $R^1$, for example, a cyclopropyl group, a cyclobutyl group, a cyclopentyl group, a cyclohexyl group, a cycloheptyl group, and a cyclooctyl group, etc. are mentioned, and a cyclopropyl group is preferable.

As the hydroxy lower alkyl group for $R^1$, for example, a hydroxymethyl group, a 1-hydroxyethyl group, a 1-hydroxypropyl group, a 2-hydroxyethyl group, a 2-hydroxypropyl group, a 2-hydroxy-1-methylethyl group, a 1-hydroxy-1-methylethyl group, a 1,2-dihydroxyethyl group, and a 3-hydroxypropyl group, etc. are mentioned, and a hydroxymethyl group is preferable.

$R^1$ is preferably a lower alkyl group (more preferably a methyl group, an ethyl group, a propyl group, or an isopropyl group, and particularly preferably a methyl group), a chlorine atom, a trifluoromethyl group, a cyclopropyl group, a cyano group, or a hydroxymethyl group.

W represents a nitrogen atom or a methine group.

W is preferably a nitrogen atom.

$L^1$ represents a halogen atom, a cyano group, a lower alkyl group, a halo-lower alkyl group, a cycloalkyl group, a lower alkoxy group, a halo-lower alkoxy group, or a hydroxy lower alkyl group.

As the halogen atom for $L^1$, for example, a fluorine atom, a chlorine atom, a bromine atom, and an iodine atom, etc. are mentioned, and a fluorine atom and a chlorine atom are preferable.

As the lower alkyl group for $L^1$, for example,
a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-3-methylpropyl group, etc. are mentioned, and
a methyl group, an ethyl group, a propyl group, and an isopropyl group, etc. are preferable, and
a methyl group is more preferable.

As the halo-lower alkyl group for $L^1$, for example, a fluoromethyl group, a difluoromethyl group, a trifluoromethyl group, a 2-fluoroethyl group, a 1,2-difluoroethyl group, a 2,2,2-trifluoroethyl group, a pentafluoroethyl group, a chloromethyl group, a 2-chloroethyl group, a 1,2-dichloroethyl group, a 2,2,2-trichloroethyl group, a bromomethyl group, and an iodomethyl group, etc. are mentioned, and a difluoromethyl group and a trifluoromethyl group are preferable, and a trifluoromethyl group is more preferable.

As the cycloalkyl group for $L^1$, for example, a cyclopropyl group, a cyclobutyl group, a cyclopentyl group, a cyclohexyl group, a cycloheptyl group, and a cyclooctyl group, etc. are mentioned, and a cyclopropyl group is preferable.

As the lower alkoxy group for $L^1$, for example, a methoxy group, an ethoxy group, a propoxy group, an isopropoxy group, a butoxy group, a sec-butoxy group, a tert-butoxy group, a pentyloxy group, an isopentyloxy group, a hexyloxy group, and an isohexyloxy group, etc. are mentioned, and a methoxy group is preferable.

As the halo-lower alkoxy group for $L^1$, for example, a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, and an iodomethoxy group, etc. are mentioned, and a difluoromethoxy group and a trifluoromethoxy group are preferable, and a trifluoromethoxy group is more preferable.

As the hydroxy lower alkyl group for $L^1$, for example, a hydroxymethyl group, a 1-hydroxyethyl group, a 1-hydroxypropyl group, a 2-hydroxyethyl group, a 2-hydroxypropyl group, a 2-hydroxy-1-methylethyl group, a 1-hydroxy-1-methylethyl group, a 1,2-dihydroxyethyl group, and a 3-hydroxypropyl group, etc. are mentioned, and a hydroxymethyl group is preferable.

$L^1$ is preferably a fluorine atom, a chlorine atom, a cyano group, a lower alkyl group (more preferably a methyl group, an ethyl group, a propyl group, or an isopropyl group, and particularly preferably a methyl group), a difluoromethyl group, a trifluoromethyl group, a cyclopropyl group, a methoxy group, a difluoromethoxy group, a trifluoromethoxy group, or a hydroxymethyl group.

$L^2$ is a halogen atom or a group represented by —OSO$_2$R$^4$.

As the halogen atom for $L^2$, for example, a fluorine atom, a chlorine atom, a bromine atom, and an iodine atom, etc. are mentioned, and a chlorine atom, a bromine atom, and an iodine atom are preferable, and an iodine atom is preferable.

R$^4$ is a lower alkyl group, a halo-lower alkyl group, or an aryl group (wherein the aryl group is optionally substituted with a halogen atom, a lower alkyl group, or a lower alkoxy group)

As the lower alkyl group for R$^4$, for example, a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-3-methylpropyl group, etc. are mentioned, and a methyl group, an ethyl group, a propyl group, and an isopropyl group, etc. are preferable, and a methyl group is more preferable.

As the halo-lower alkyl group for R$^4$, for example, a fluoromethyl group, a difluoromethyl group, a trifluoromethyl group, a 2-fluoroethyl group, a 1,2-difluoroethyl group, a 2,2,2-trifluoroethyl group, a pentafluoroethyl group, a chloromethyl group, a 2-chloroethyl group, a 1,2-dichloroethyl group, a 2,2,2-trichloroethyl group, a bromomethyl group, and an iodomethyl group, etc. are mentioned, and a trifluoromethyl group and a pentafluoroethyl group are preferable.

As the aryl group for R$^4$, for example, a phenyl group, a naphthyl group, a biphenyl group, and an anthryl group, etc. are mentioned, and a phenyl group is preferable.

The aryl group of R$^4$ is optionally substituted with a halogen atom, a lower alkyl group, or a lower alkoxy group.

As the "aryl groups substituted with a halogen atom, a lower alkyl group, or a lower alkoxy group" for R$^4$, for example, a 2-fluorophenyl group, a 3-fluorophenyl group, a 4-fluorophenyl group, a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, and a 4-methoxyphenyl group, etc. are mentioned.

Therefore, $L^2$ is, for example, a chlorine atom, a bromine atom, an iodine atom, a methylsulfonyloxy group, an ethylsulfonyloxy group, a 1-propylsulfonyloxy group, an isopropylsulfonyloxy group, a trifluoromethylsulfonyloxy group, a pentafluoroethylsulfonyloxy group, a phenylsulfonyloxy group, a 2-methylphenylsulfonyloxy group, a 3-methylphenylsulfonyloxy group, a 4-methylphenylsulfonyloxy group, a 2-methoxyphenylsulfonyloxy group, a 3-methoxyphenylsulfonyloxy group, and a 4-methoxyphenylsulfonyloxy group, etc. are mentioned, and a chlorine atom, a bromine atom, an iodine atom, a methylsulfonyloxy group, an ethylsulfonyloxy group, a tri-fluoromethylsulfonyloxy group, a phenylsulfonyloxy group, and a 4-methylphenylsulfonyloxy group, etc. are preferable.

$L^2$ is preferably a chlorine atom, a bromine atom, or an iodine atom, and more preferably an iodine atom.

LG is a halogen atom or a group represented by —OSO$_2$R$^5$.

As the halogen atom for LG, for example, a fluorine atom, a chlorine atom, a bromine atom, and an iodine atom, etc. are mentioned, and a chlorine atom, a bromine atom, and an iodine atom are preferable, and a chlorine atom is more preferable.

R$^5$ represents a lower alkyl group, a halo-lower alkyl group, or an aryl group (wherein the aryl group is optionally substituted with a halogen atom, a lower alkyl group, or a lower alkoxy group).

As the lower alkyl group for R$^5$, for example, a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-3-methylpropyl group, etc. are mentioned, and a methyl group, an ethyl group, a propyl group, and an isopropyl group, etc. are preferable, and a methyl group is more preferable.

As the halo-lower alkyl group for R$^5$, for example, a fluoromethyl group, a difluoromethyl group, a trifluoromethyl group, a 2-fluoroethyl group, a 1,2-difluoroethyl group, a 2,2,2-trifluoroethyl group, a pentafluoroethyl group, a chloromethyl group, a 2-chloroethyl group, a 1,2-dichloroethyl group, a 2,2,2-trichloroethyl group, a bromomethyl group, and an iodomethyl group, etc are mentioned, and a trifluoromethyl group is preferable.

As the aryl group for R$^5$, for example, a phenyl group, a naphthyl group, a biphenyl group, and an anthryl group, etc are mentioned, and a phenyl group is preferable.

The aryl group for R$^5$ is optionally substituted with a halogen atom, a lower alkyl group, or a lower alkoxy group.

As the "aryl groups substituted with a halogen atom, a lower alkyl group, or a lower alkoxy group" for R$^5$, for example, a 2-fluorophenyl group, a 3-fluorophenyl group, a 4-fluorophenyl group, a 2-chlorophenyl group, a 3-chlorophenyl group, a 4-chlorophenyl group, a 2-methylphenyl group, a 3-methylphenyl group, a 4-methylphenyl group, a 2-methoxyphenyl group, a 3-methoxyphenyl group, and a 4-methoxyphenyl group, etc. are mentioned.

Therefore, LG is, for example, a chlorine atom, a bromine atom, an iodine atom, a methylsulfonyloxy group, an ethylsulfonyloxy group, a 1-propylsulfonyloxy group, an isopropylsulfonyloxy group, a trifluoromethylsulfonyloxy group, a pentafluoroethylsulfonyloxy group, a phenylsulfonyloxy group, a 2-methylphenylsulfonyloxy group, a 3-methylphenylsulfonyloxy group, a 4-methylphenylsulfonyloxy group, a 2-methoxyphenylsulfonyloxy group, a 3-methoxyphenylsulfonyloxy group, and a 4-methoxyphenylsulfonyloxy group, etc are mentioned, and a chlorine atom, a bromine atom, an iodine atom, a methylsulfonyloxy group, an ethylsulfonyloxy group, a trifluoromethylsulfonyloxy group, a phenylsulfonyloxy group, and a 4-methylphenylsulfonyloxy group, etc. are preferable.

$X_L$ is a halogen atom.

As the halogen atom for $X_L$, for example, a fluorine atom, a chlorine atom, a bromine atom, and an iodine atom, etc. are mentioned, and a chlorine atom, a bromine atom, and an iodine atom are preferable, and an iodine atom is preferable.

$R^2$ represents a lower alkyl group, a halo-lower alkyl group, a cycloalkyl group, a lower alkenyl group, or an aralkyl group.

As the lower alkyl group for $R^2$, for example, a methyl group, an ethyl group, a propyl group, an isopropyl group, a butyl group, an isobutyl group, a sec-butyl group, a tert-butyl group, a pentyl group, an isopentyl group, an isoamyl group, a neopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, and a 1-ethyl-3-methylpropyl group, etc. are mentioned, and a methyl group, an ethyl group, a propyl group, an isopropyl group, and a tert-butyl group, etc. are preferable, and a methyl group and an ethyl group are more preferable.

As the halo-lower alkyl group for $R^2$, for example, a fluoromethyl group, a difluoromethyl group, a trifluoromethyl group, a 2-fluoroethyl group, a 1,2-difluoroethyl group, a 2,2,2-trifluoroethyl group, a pentafluoroethyl group, a chloromethyl group, a 2-chloroethyl group, a 1,2-dichloroethyl group, a 2,2,2-trichloroethyl group, a bromomethyl group, and an iodomethyl group, etc are mentioned, and a 2,2,2-trichloroethyl group is preferable.

As the cycloalkyl group for $R^2$, for example, a cyclopropyl group, a cyclobutyl group, a cyclopentyl group, a cyclohexyl group, a cycloheptyl group, and a cyclooctyl group, etc are mentioned, and a cyclopropyl group is preferable.

As the lower alkenyl group for $R^2$, for example, a vinyl group, a 1-propenyl group, an allyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, and a 4-pentenyl group, etc are mentioned, and a vinyl group and an allyl group are preferable.

As the aralkyl group for $R^2$, for example, a benzyl group, a 1-phenylethyl group, a 2-phenylethyl group, a 1-naphthylmethyl group, and a 2-naphthylmethyl group, etc are mentioned, and a benzyl group is preferable.

$R^2$ is preferably a methyl group, an ethyl group, a propyl group, an isopropyl group, a tert-butyl group, a 2,2,2-trichloroethyl group, a cyclopropyl group, a vinyl group, an allyl group, or a benzyl group.

$R^2$ is more preferably a methyl group, an ethyl group, a propyl group, an isopropyl group, or a tert-butyl group, and particularly preferably a methyl group or an ethyl group.

$R^3$ represents a chlorine atom, a bromine atom, or an iodine atom.

The compound used in the present invention may have an asymmetric center, a chiral axis, and a chiral plane.

The compound used in the present invention may be produced as a racemate, as a racemic mixture, and as an individual diastereomer.

In addition, all the possible isomers including optical isomers and mixtures thereof are all encompassed by the present invention.

Further, compounds disclosed herein may also be present as tautomers. Even in the case where only one tautomer structure is described, it is intended that both tautomer forms are encompassed by the scope of the present invention.

Next, the method of the present invention will be specifically described. Incidentally, in order to promote the progress of the reaction, reagents other than the exemplified reagents can be appropriately used. For the heating in each reaction, as necessary, microwave irradiation may be conducted. In addition, raw material compounds not described for the production methods are commercially available compounds, or compounds that can be easily prepared by combining known synthesis reactions.

The compound obtained in each step can be isolated and purified by a commonly used, conventional method such as crystallization or recrystallization. However, in some cases, the compound can proceed to the next step without isolation/purification.

In the following production method, "room temperature" means from 1 to 40° C.

The production method of the present invention is a process of producing, from a compound represented by formula (1) (hereinafter also referred to as compound (1); the same applies to the compound represented by each formula), a difluoromethylene compound represented by formula (9) (compound (9)) through a multiple steps (steps (A) to (F)).

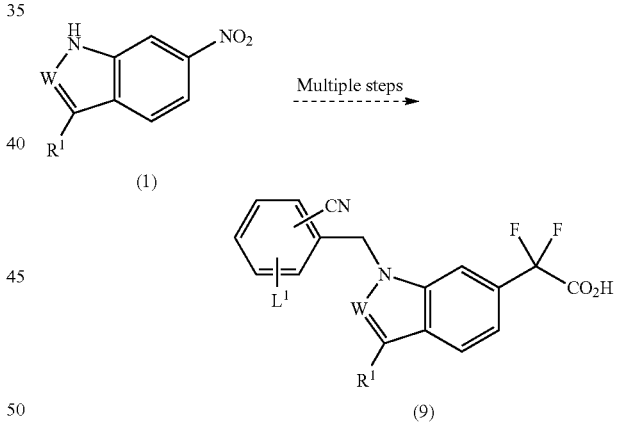

[Step (A)]

The step (A) is a step of allowing a compound (1) to react with a compound represented by formula (2) (compound (2)) to give a compound represented by formula (3) (compound (3)).

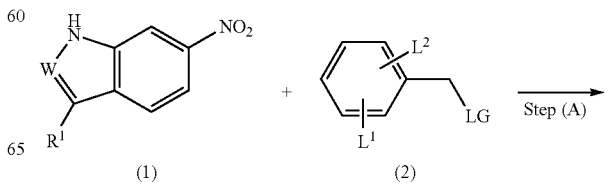

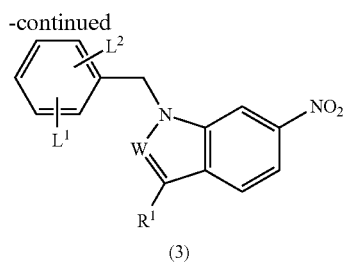

(3)

The amount of compound (2) is usually 1 to 3 mol, preferably 1 to 1.3 mol, and more preferably 1 to 1.1 mol with respect to 1 mol of the compound (1).

The step (A) is preferably performed in the presence of a base.

As the base used, for example, sodium carbonate, potassium carbonate, cesium carbonate, sodium hydrogen carbonate, cesium fluoride, sodium hydride, potassium tert-butoxide, lithium hydroxide, sodium hydroxide, and potassium hydroxide, etc. are mentioned, and potassium carbonate, cesium carbonate, sodium hydride, and potassium hydroxide, etc. are preferable, and potassium carbonate and cesium carbonate are more preferable.

The amount of base is usually 1 to 3 mol, preferably 1 to 2 mol, and more preferably 1 to 1.5 mol with respect to 1 mol of the compound (1).

The reaction temperature is usually 0° C. to 60° C., preferably 5° C. to 50° C., and more preferably 10° C. to 40° C.

The reaction time is usually 1 hour to 24 hours, and preferably 1 hour to 6 hours.

The reaction solvent is not particularly limited as long as it does not interfere with the reaction, and solvents such as N,N-dimethylformamide, N,N-dimethylacetamide, N-methyl-2-pyrrolidone, dimethyl sulfoxide, chloroform, dichloromethane, tetrahydrofuran, 2-methyltetrahydrofuran, 1,4-dioxane, 1,2-dimethoxyethane, methyl tert-butyl ether, ethyl acetate, methyl acetate, propyl acetate, acetone, methyl ethyl ketone, and acetonitrile, etc. are mentioned, and N,N-dimethylformamide, N,N-dimethylacetamide, and N-methyl-2-pyrrolidone are preferable, and N,N-dimethylformamide is more preferable.

Specific examples of compounds (1) include 3-methyl-6-nitroindole, 3-ethyl-6-nitroindole, 3-methyl-6-nitro-1H-indazole, 3-ethyl-6-nitro-1H-indazole, 3-propyl-6-nitro-H-indazole, 3-isopropyl-6-nitro-1H-indazole, 3-cyclopropyl-6-nitro-1H-indazole, 3-chloro-6-nitro-1H-indazole, 3-iodo-6-nitro-1H-indazole, 6-nitro-3-trifluoromethyl-1H-indazole, and the like.

The compound (1) can be a commercially available product, or can be obtained by a suitable combination of the known methods or the methods described in Examples or similar methods as necessary.

Specific examples of compounds (2) include 1-(chloromethyl)-2-iodo-3-methylbenzene, 1-(chloromethyl)-2-iodo-4-methylbenzene, 2-(chloromethyl)-1-iodo-4-methylbenzene, 2-(chloromethyl)-1-iodo-3-methylbenzene, 1-(chloromethyl)-3-iodo-2-methylbenzene, 4-(chloromethyl)-2-iodo-1-methylbenzene, 1-(chloromethyl)-3-iodo-5-methylbenzene, 2-(chloromethyl)-4-iodo-1-methylbenzene, 1-(chloromethyl)-4-iodo-2-methylbenzene, 4-(chloromethyl)-2-iodo-methylbenzene, 4-(chloromethyl)-1-iodo-2-methylbenzene, 2-bromo-1-(chloromethyl)-3-methylbenzene, 2-bromo-1-(chloromethyl)-4-methylbenzene, 1-bromo-2-(chloromethyl)-4-methylbenzene, 1-bromo-2-(chloromethyl)-3-methylbenzene, 1-bromo-3-(chloromethyl)-2-methylbenzene, 2-bromo-4-(chloromethyl)-1-methylbenzene, 1-bromo-3-(chloromethyl)-5-methylbenzene, 4-bromo-2-(chloromethyl)-1-methylbenzene, 4-bromo-1-(chloromethyl)-2-methylbenzene, 1-bromo-4-(chloromethyl)-2-methylbenzene, 2-(chloromethyl)-1-fluoro-3-iodobenzene, 1-chloro-2-(chloromethyl)-3-iodobenzene, 1-bromo-2-(chloromethyl)-3-iodobenzene, 2-(chloromethyl)-1-ethyl-3-iodobenzene, 2-(chloromethyl)-1-iodo-3-propylbenzene, 2-(chloromethyl)-1-iodo-3-isopropylbenzene, 2-(chloromethyl)-1-iodo-3-(trifluoromethyl)benzene, 2-(chloromethyl)-1-cyclopropyl-3-iodobenzene, 2-(chloromethyl)-1-iodo-3-methoxybenzene, 2-(chloromethyl)-1-iodo-3-(trifluoromethoxy)benzene, 3-bromo-2-(chloromethyl)benzonitrile, 1-bromo-2-(chloromethyl)-3-fluorobenzene, 1-bromo-3-chloro-2-(chloromethyl)benzene, 1-bromo-2-(chloromethyl)-3-methoxybenzene, 2-(bromomethyl)-1-iodo-3-methylbenzene, 1-bromo-2-(bromomethyl)-3-methylbenzene, 1-iodo-2-(iodomethyl)-3-methylbenzene, and the like.

The compound (2) can be a commercially available product, or can be obtained by a suitable combination of the known methods or the methods described in Examples or similar methods as necessary.

When a compound represented by formula (1) wherein W is a nitrogen atom (compound (1-1)) is subjected to an alkylation reaction with the compound (2), together with a compound represented by formula (3-1a) (compound (3-1a)), a compound represented by formula (3-1b) (compound (3-1b)) may be obtained as a mixture.

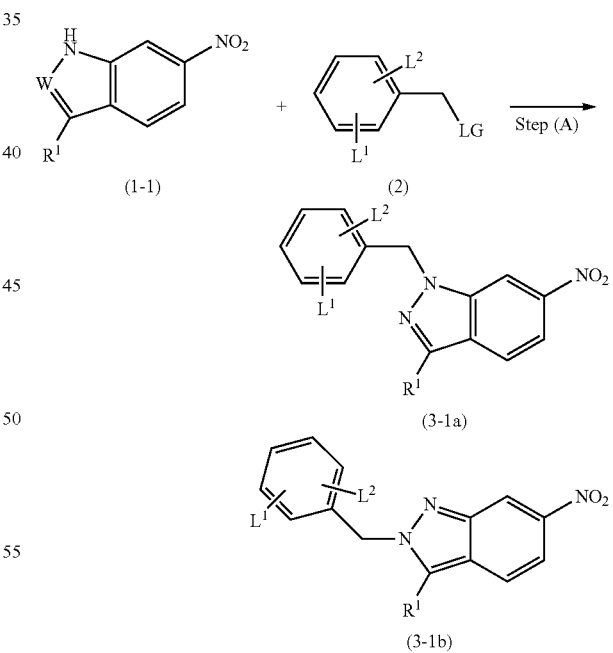

In this case, it is preferable that the above-mentioned mixture is further subjected to a purification step (step (A-2)) to isolate the compound (3-1a) for use in the next step (B).

As a preferred example of the step (A-2), a recrystallization step can be mentioned.

Examples of recrystallization solvents used in the step (A-2) include solvents such as ethyl acetate, methyl acetate, isopropyl acetate, n-hexane, n-pentane, n-heptane, diisopropyl ether, methyl tert-butyl ether, methanol, ethanol, propanol, isopropanol, butanol, tetrahydrofuran, 2-methyltetrahydrofuran, acetone, methyl ethyl ketone, acetonitrile, N,N-dimethylformamide, N,N-dimethylacetamide, water, and the like.

The recrystallization solvent can be used as a single solvent, or a combination of two or more solvents (mixed solvent).

Preferred examples of combinations of recrystallization solvents include a combination of ethyl acetate and n-hexane, a combination of tetrahydrofuran and methanol, a combination of 2-methyltetrahydrofuran and methanol, a combination of tetrahydrofuran and ethanol, a combination of tetrahydrofuran and propanol, a combination of tetrahydrofuran and isopropanol, a combination of acetone and methanol, a combination of acetone and ethanol, a combination of acetone and propanol, a combination of acetone and isopropanol, a combination of acetonitrile and methanol, a combination of acetonitrile and ethanol, a combination of acetonitrile and propanol, a combination of acetonitrile and isopropanol, a combination of N,N-dimethylformamide and methanol, a combination of N,N-dimethylformamide and ethanol, a combination of N,N-dimethylformamide and propanol, a combination of N,N-dimethylformamide and isopropanol, a combination of tetrahydrofuran and heptane, a combination of tetrahydrofuran and diisopropyl ether, a combination of tetrahydrofuran and methyl tert-butyl ether, a combination of tetrahydrofuran and methyl ethyl ketone, a combination of tetrahydrofuran and water, and the like.

As a more preferred combination of recrystallization solvents, a combination of tetrahydrofuran and methanol can be mentioned.

In the case where the recrystallization solvent is a combination of tetrahydrofuran and methanol, the amount of each solvent is usually 1 mL to 100 mL of tetrahydrofuran/1 mL to 100 mL of methanol, more preferably 5 mL to 10 mL of tetrahydrofuran/5 mL to 40 mL of methanol, and particularly preferably 7.5 mL of tetrahydrofuran/12.5 mL of methanol with respect to 1 gram of the obtained crude material.

The temperature of recrystallization in the step (A-2) is preferably 70° C. to −10° C., and more preferably 65° C. to 0° C.

[Step (B)]

The step (B) is a step of cyanating $L^2$ of the compound (3) to give a compound represented by formula (4) (compound (4)).

The cyanating agent used in the step (B) is not particularly limited as long as it can react with the compound (3) to produce a compound (4), and examples thereof include potassium cyanide, sodium cyanide, zinc cyanide, copper cyanide, potassium ferrocyanide, and the like, and zinc cyanide, copper cyanide, potassium ferrocyanide, and the like are preferable, and zinc cyanide and copper cyanide are more preferable.

The amount of cyanating agent is usually 0.5 to 3 mol, preferably 0.6 to 2.5 mol, and more preferably 0.9 to 2 mol with respect to 1 mol of the compound (3).

The step (B) is preferably performed, as necessary, in the presence of a palladium catalyst or a combination of a palladium catalyst and a phosphine ligand. In particular, in the case where zinc cyanide is used as a cyanating agent, the step (B) is preferably performed in the presence of a palladium catalyst or a combination of a palladium catalyst and a phosphine ligand.

Examples of palladium catalysts include $Pd(PPh_3)_4$, $Pd(OAc)_2$, $Pd(TFA)_2$, $Pd(dba)_2$, $Pd_2(dba)_3$, $PdCl_2(PPh_3)_4$, and the like.

The amount of palladium catalyst is usually 0.001 to 0.5 mol, preferably 0.005 to 0.1 mol, and more preferably 0.01 to 0.1 mol with respect to 1 mol of the compound (3).

Examples of phosphine ligands include triphenylphosphine, tri(2-methylphenyl)phosphine, tri-tert-butylphosphine, 2-(di-tert-butylphosphino)biphenyl, 2-di-tert-butylphosphino-2'-(N,N-dimethylamino)biphenyl, 2-(dicyclohexylphosphino)biphenyl, 2-dicyclohexylphosphino-2',6'-dimethoxybiphenyl, 2-dicyclohexylphosphino-2',4',6'-triisopropylbiphenyl, 2-dicyclohexylphosphino-2'-(N,N-dimethylamino) biphenyl, (S)-(−)-2,2'-bis(diphenylphosphino)-1,1'-binaphthyl, (R)-(+)-2,2'-bis(diphenylphosphino)-1,1'-binaphthyl, (±)-2,2'-bis(diphenylphosphino)-1,1'-binaphthyl, and the like.

The reaction temperature is usually 0° C. to 100° C., preferably 70° C. to 90° C., and more preferably 70° C. to 85° C.

The reaction time is usually 1 hour to 24 hours, and preferably 3 hours to 6 hours.

The reaction solvent is not particularly limited as long as it does not interfere with the reaction, and solvents such as N,N-dimethylformamide, N,N-dimethylacetamide, N-methyl-2-pyrrolidone, chloroform, dichloromethane, tetrahydrofuran, 2-methyltetrahydrofuran, 1,4-dioxane, 1,2-dimethoxyethane, acetone, methyl ethyl ketone, acetonitrile, and the like are mentioned, and N,N-dimethylformamide, N,N-dimethylacetamide, and N-methyl-2-pyrrolidone are preferable, and N,N-dimethylformamide is more preferable.

In the case where copper cyanide is used as a cyanating agent, proline may be further added to perform the step (B).

In this case, the amount of copper cyanide is usually 1 to 10 mol, preferably 1 to 3 mol with respect to 1 mol of the compound (3).

In addition, the amount of proline is usually 0.1 to 10 mol, preferably 0.5 to 2 mol with respect to 1 mol of the compound (3).

The reaction temperature is usually 0° C. to 120° C., preferably 80° C. to 120° C., and more preferably 100° C. to 120° C.

The reaction time is usually 1 hour to 24 hours, and preferably 2 hours to 6 hours.

The reaction solvent is not particularly limited as long as it does not interfere with the reaction, and solvents such as N,N-dimethylformamide, N,N-dimethylacetamide, N-methyl-2-pyrrolidone, chloroform, dichloromethane, tet-

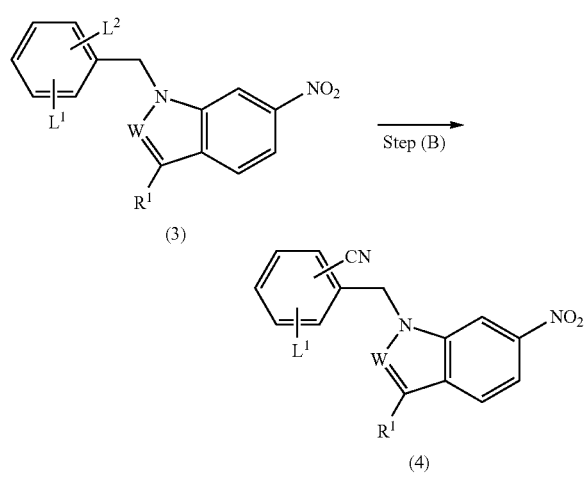

rahydrofuran, 2-methyltetrahydrofuran, 1,4-dioxane, 1,2-dimethoxyethane, acetone, methyl ethyl ketone, acetonitrile, and the like are mentioned, and N,N-dimethylformamide, N,N-dimethylacetamide, and N-methyl-2-pyrrolidone are preferable, and N,N-dimethylformamide is more preferable.

The compound (4) obtained in the step (B) can be easily isolated by a known procedure such as concentration, solvent extraction, or crystallization, and can be obtained with more high purity by recrystallization.

The obtained high-purity compound (4) may be used in the next step (C).

[Step (C)]

The step (C) is a step of reducing a nitro group of the compound (4) to give a compound represented by formula (5) (compound (5)).

The reduction reaction of the step (C) is not particularly limited as long as the nitro group of the compound (4) is reduced to produce a compound (5), and examples thereof include reduction using a metal hydride (e.g., lithium aluminum hydride, etc.);

reduction using a metal salt (e.g., tin chloride, etc.);

reduction using a metal (e.g., zinc, tin, iron, etc.) under acidic conditions;

reduction using a metal salt (e.g., tin chloride, etc.) under acidic conditions;

reduction using a metal (e.g., zinc, etc.) under basic conditions; and hydrogenation using a catalyst (e.g., platinum, Raney nickel, palladium carbon, a ruthenium complex, etc.).

Incidentally, the metal salt may be a hydrate (e.g., tin chloride dihydrate).

Among these reduction reactions, reduction using a metal salt (e.g., tin chloride);

reduction using a metal (e.g., zinc, tin, iron, etc.) under acidic conditions;

reduction using a metal salt (e.g., tin chloride, tin chloride dihydrate, etc.) under acidic conditions;

hydrogenation using a catalyst (e.g., platinum, Raney nickel, palladium carbon, a ruthenium complex, etc.); and the like are preferable, and reduction using a metal salt (e.g., tin chloride, tin chloride dihydrate, etc.) under acidic conditions is more preferable.

Examples of acids used under acidic conditions include hydrochloric acid, sulfuric acid, acetic acid, and the like.

The amount of reducing agent is usually 1 to 6 mol, preferably 1 to 5 mol, and more preferably 1 to 4 mol with respect to 1 mol of the compound (4).

The amount of acid is usually 1 to 30 mol, preferably 1 to 20 mol, and more preferably 1 to 15 mol with respect to 1 mol of the compound (4).

The reaction temperature is usually 0° C. to 100° C., preferably 10° C. to 60° C., and more preferably 15° C. to 40° C.

The reaction time is usually 1 hour to 24 hours, and preferably 3 hours to 23 hours.

The reaction solvent is not particularly limited as long as it does not interfere with the reaction, and examples thereof include solvents such as ethyl acetate, methyl acetate, propyl acetate, methanol, ethanol, propanol, isopropanol, tetrahydrofuran, 2-methyltetrahydrofuran, 1,2-dimethoxyethane, water, and the like, and methanol and ethanol are preferable, and methanol is more preferable.

The product of the step (C) may be a salt of the compound (5).

As salts of the compound (5), salts of acid addition salts at the amino group of the compound (5) can be mentioned.

Examples of acid addition salts include inorganic acid salts (e.g., hydrochloride, hydrobromide, sulfate, nitrate, phosphate, perchlorate, sulfamate, etc.);

organic carboxylic acid salts (e.g., formate, acetate, trifluoroacetate, maleate, fumarate, tartrate, citrate, succinate, malate, ascorbate, etc.);

organic sulfonic acid salts (e.g., methanesulfonate, isethionate, benzenesulfonate, p-toluenesulfonate, etc.);

acidic amino acid salts (e.g., aspartate, glutamate, etc.); and the like, and inorganic acid salts such as hydrochloride, sulfate, nitrate, phosphate, and perchlorate are preferable, and hydrochloride is more preferable.

A salt of the compound (5) can be obtained by a suitable combination of methods commonly used in the field of synthetic organic chemistry. Specifically, a solvent is added to a compound (5), and an acid is added thereto, whereby a salt of the compound (5) can be obtained.

The amount of acid is usually 1 to 3 mol, preferably 1 to 2 mol, and more preferably 1 to 1.3 mol with respect to 1 mol of the compound (5).

The reaction temperature is usually 0° C. to 60° C., preferably 10° C. to 40° C., and more preferably 15° C. to 30° C.

The reaction time is usually 1 hour to 24 hours, and preferably 1 hour to 12 hours.

The reaction solvent is not particularly limited as long as it does not interfere with the reaction, and examples thereof include ethyl acetate, methyl acetate, propyl acetate, methanol ethanol, propanol, isopropanol, tetrahydrofuran, 2-methyltetrahydrofuran, 1,4-dioxane, 1,2-dimethoxyethane, water, and the like, and preferably, ethyl acetate.

The compound (5) or salt thereof obtained in the step (C) can be easily isolated by a known procedure such as concentration, solvent extraction, or crystallization, and can be obtained in high purity by recrystallization. The obtained high-purity compound (5) or salt thereof may be used in the next step (D).

[Step (D)]

The step (D) is a step of halogenating an amino group of the compound (5) or salt thereof to give a compound represented by formula (6) (compound (6)).

Specifically, the amino group of the compound (5) or salt thereof is subjected to Sandmeyer Reaction, that is, a diazotization reaction and following halogenation of the formed diazo group, thereby giving a compound (6).

(5)

(6)

The diazotization reaction is usually performed using a diazotizing agent.

Examples of diazotizing agents include
nitrous acid;
nitrites (e.g., sodium nitrite, potassium nitrite, etc.); and
nitrite esters (e.g., ethyl nitrite, butyl nitrite, amyl nitrite, isoamyl nitrite, etc.).

In addition, it is also possible to use a nitrosyl halogenide (nitrosyl chloride, etc.).

Incidentally, in the case where a nitrite is used as a diazotizing agent, the reaction usually takes place under acidic conditions. Examples of acids used under acidic conditions include hydrochloric acid, sulfuric acid, and the like, preferably, hydrochloric acid.

As a diazotizing agent, a nitrite (sodium nitrite, etc.) is preferable.

The amount of diazotizing agent is usually 1 to 10 mol, preferably 1 to 3 mol, and more preferably 1 to 1.1 mol with respect to 1 mol of the compound (5) or salt thereof.

The halogenation of a diazo group can be performed, for example, (i) in the presence of a copper halide, (ii) in the presence of hydrochloric acid or hydrobromic acid and a copper powder or a copper salt, or (iii) in the presence of an iodide salt.

Examples of copper halides include copper(I) chloride, copper(I) bromide, copper(I) iodide, copper(II) chloride, copper(II) bromide, copper(II) iodide, and the like.

Examples of copper salts include copper sulfate, copper carbonate, copper oxide, and the like.

Examples of iodide salts include sodium iodide, potassium iodide, tetrabutylammonium iodide, and the like.

The amount of copper halide, copper powder, or copper salt is usually 0.001 to 20 mol with respect to 1 mol of the compound (5).

The amount of iodide salt is usually 1 to 10 mol, preferably 1 to 3 mol, and more preferably 1 to 1.5 mol with respect to 1 mol of the compound represented by formula (5).

The reaction temperature is usually −20° C. to 100° C., preferably −15° C. to 40° C., and more preferably −10° C. to 25° C.

The reaction time is usually 1 hour to 24 hours, and preferably 1 hour to 19 hours.

In addition, the reaction time may be usually 15 minutes to 24 hours, and preferably 15 minutes to 19 hours.

The reaction solvent is not particularly limited as long as it does not interfere with the reaction, and examples thereof include acetonitrile, ethyl acetate, methyl acetate, propyl acetate, methanol, ethanol, propanol, isopropanol, butanol, methoxyethanol, diethyl ether, diisopropyl ether, tetrahydrofuran, 2-methyltetrahydrofuran, 1,4-dioxane, 1,2-dimethoxyethane, acetone, dimethyl sulfoxide, phosphoric acid, acetic acid, water, and the like.

It is also possible to use a mixture of two or more solvents in suitable proportions.

As a reaction solvent, a mixed solvent of acetonitrile and water is preferable.

The compound (6) obtained in step (D) can be easily isolated by a known procedure such as concentration, solvent extraction, or crystallization, and can be obtained in high purity by recrystallization. The obtained high-purity compound (6) may be used in the next step (E).

[Step (E)]

The step (E) is a step of subjecting the compound (6) to a coupling reaction with a compound represented by formula (7) (compound (7)) to give a compound represented by formula (8) (compound (8)).

(6)

(7)

(8)

In the compound (7), $R^2$ is preferably a lower alkyl group.

Specific example of compounds (7) include methyl bromodifluoroacetate, ethyl bromodifluoroacetate, propyl bromodifluoroacetate, isopropyl bromodifluoroacetate, tert-butyl bromodifluoroacetate, methyl chlorodifluoroacetate, ethyl chlorodifluoroacetate, propyl chlorodifluoroacetate, isopropyl chlorodifluoroacetate, tert-butyl chlorodifluoroacetate, methyl difluoroiodoacetate, ethyl difluoroiodoacetate, isopropyl difluoroiodoacetate, and the like, and preferably, methyl bromodifluoroacetate and ethyl bromodifluoroacetate.

The amount of compound (7) is usually 1 to 10 mol, preferably 1 to 5 mol, and more preferably 1 to 3 mol with respect to 1 mol of the compound (6).

The amount of copper is usually 1 to 20 mol, preferably 1 to 10 mol, and more preferably 1 to 9 mol with respect to 1 mol of the compound (6).

The reaction temperature is usually 0° C. to 70° C., preferably 0° C. to 40° C., and more preferably 20° C. to 40° C.

The reaction time is usually 1 hour to 24 hours, preferably 2 hours to 12 hours, and more preferably 4 hours to 8 hours.

The reaction solvent is not particularly limited as long as it does not interfere with the reaction, and examples thereof include solvents such as dimethyl sulfoxide, N,N-dimethylformamide, N,N-dimethylacetamide, N-methyl-2-pyrrolidone, tetrahydrofuran, 2-methyltetrahydrofuran, 1,4-dioxane, 1,2-dimethoxyethane, and the like.

It is also possible to use a mixture of two or more solvents in suitable proportions.

As a reaction solvent, dimethyl sulfoxide or a mixed solvent of dimethyl sulfoxide and tetrahydrofuran is preferable.

The ratio (volume ratio) in a mixed solvent of dimethyl sulfoxide and tetrahydrofuran is usually dimethyl sulfoxide/tetrahydrofuran=10/1 to 1/1, preferably dimethyl sulfoxide/tetrahydrofuran=5/1 to 2/1, and more preferably dimethyl sulfoxide/tetrahydrofuran=3.5/1 to 2.5/1.

The compound (8) obtained in step (E) can be easily isolated by a known procedure such as concentration, solvent extraction, or crystallization, and can be obtained in high purity by recrystallization. The obtained high-purity compound (8) may be used in the next step (F).

Incidentally, in the case where $R^2$ of the compound (8) obtained in the step (E) is a group other than a methyl group (e.g., ethyl group), it is preferable that the $R^2$ of the compound (8) can be transesterified to a methyl group through the step (E-1) shown below, and the compound (8) can be easily isolated by crystallization.

That is, the step (E-1) is a step of transesterifying the substituent $R^2$ of the compound (8) in the presence of an acid or a base, thereby giving a compound represented by formula (8) wherein $R^2$ is a methyl group (referred to as compound (8-1)).

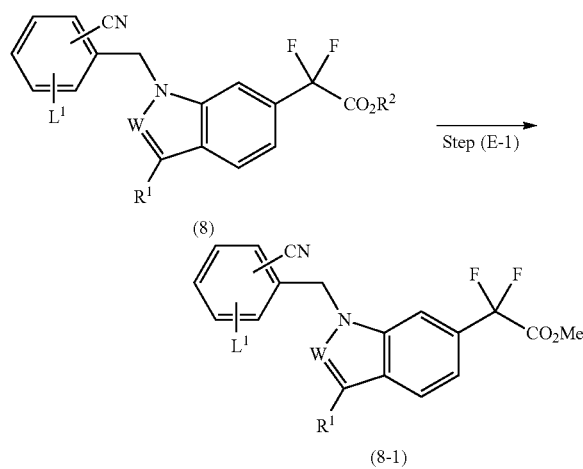

Examples of acids used in the step (E-1) include inorganic acids (e.g., hydrochloric acid, sulfuric acid, nitric acid, phosphoric acid, boric acid, etc.), organic carboxylic acids (e.g., formic acid, acetic acid, propionic acid, trifluoroacetic acid, etc.), and organic sulfonic acids (e.g., methanesulfonic acid, benzenesulfonic acid, p-toluenesulfonic acid, trifluoromethanesulfonic acid, etc.).

The amount of acid used in the step (E-1) is usually 0.01 to 10 mol, preferably 0.1 to 1 mol with respect to 1 mol of the compound (8).

Examples of bases used in the step (E-1) include inorganic bases (e.g., lithium hydroxide, potassium hydroxide, sodium hydroxide, magnesium hydroxide, calcium hydroxide, etc.) and basic salts (e.g., potassium carbonate, sodium carbonate, cesium carbonate, potassium hydrogen carbonate, sodium hydrogen carbonate, etc.)

The amount of base used in the step (E-1) is usually 0.1 to 10 mol, preferably 0.1 to 5 mol with respect to 1 mol of the compound (8).

The reaction temperature in the step (E-1) is usually −20° C. to 120° C., preferably 0° C. to 80° C., and more preferably 10° C. to 70° C.

The reaction time in the step (E-1) is usually 30 minutes to 24 hours, preferably 30 minutes to 12 hours, and more preferably 1 hour to 6 hours.

Examples of reaction solvents used in the step (E-1) include methanol.

The reaction solvent may also be a combination of methanol and other solvents as necessary.

Reaction solvents that may be combined with methanol are not particularly limited as long as they do not interfere with the reaction, and examples thereof include benzene, toluene, xylene, chlorobenzene, dichloromethane, chloroform, diethyl ether, tetrahydrofuran, 2-methyltetrahydrofuran, 1,4-dioxane, 1,2-dimethoxyethane, N,N-dimethylformamide, N,N-dimethylacetamide, acetic acid, water, and the like.

The compound (8-1) obtained in the step (E-1) is an example of the compound (8), and thus can be used in the next step (F) like the compound (8). In addition, the compound (8-1) may also be isolated by a known procedure such as concentration, solvent extraction, or crystallization, recrystallized, and then subjected to the next step (F).

[Step (F)]

The step (F) is a step of removing the substituent $R^2$ of the compound (8) to give a compound represented by formula (9) (compound (9)).

The removal of $R^2$ can be performed using various reactions depend on $R^2$ (hydrolysis reaction, deallylation reaction using a metal catalyst such as palladium or the like, chemical reduction using a metal hydride complex or the like, catalytic reduction using a palladium-carbon catalyst or a Raney nickel catalyst, etc.), however, is preferably performed by hydrolysis in the presence of an acid or a base.

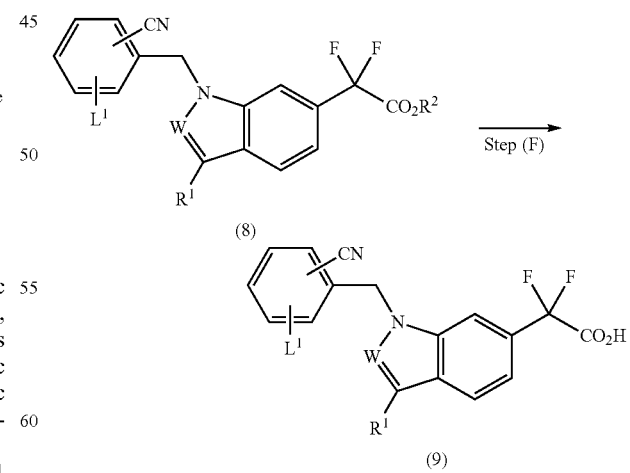

Examples of acids include inorganic acids (e.g., hydrochloric acid, sulfuric acid, nitric acid, phosphoric acid, boric acid, etc.), organic carboxylic acids (e.g., formic acid, acetic acid, propionic acid, trifluoroacetic acid, etc.), organic sulfonic acids (e.g., methanesulfonic acid, benzenesulfonic acid, p-toluenesulfonic acid, trifluoromethanesulfonic acid, etc.), and the like.

The amount of acid used is usually 0.1 to 10 mol, preferably 0.1 to 5 mol with respect to 1 mol of the compound (8).

Examples of bases include inorganic bases (e.g., lithium hydroxide, potassium hydroxide, sodium hydroxide, magnesium hydroxide, calcium hydroxide, etc.) and basic salts (e.g., potassium carbonate, sodium carbonate, cesium carbonate, potassium hydrogen carbonate, sodium hydrogen carbonate, etc.)

The amount of base used is usually 0.1 to 10 mol, preferably 0.1 to 5 mol with respect to 1 mol of the compound (8).

The reaction temperature is usually −20° C. to 100° C., preferably 0° C. to 50° C., and more preferably 10° C. to 30° C.

The reaction time is usually 30 minutes to 24 hours, preferably 30 minutes to 6 hours, and more preferably 30 minutes to 4 hours.

The reaction solvent is not particularly limited as long as it does not interfere with the reaction, and examples thereof include methanol, ethanol, propanol, isopropanol, butanol, benzene, toluene, xylene, chlorobenzene, dichloromethane, chloroform, diethyl ether, tetrahydrofuran, 2-methyltetrahydrofuran, 1,4-dioxane, 1,2-dimethoxyethane, N,N-dimethylformamide, N,N-dimethylacetamide, acetic acid, water, and the like.

It is also possible to use a mixture of two or more solvents in suitable proportions.

Preferred examples of reaction solvents include methanol, ethanol, tetrahydrofuran, 2-methyltetrahydrofuran, a mixed solvent of methanol and water, a mixed solvent of ethanol and water, a mixed solvent of tetrahydrofuran and water, a mixed solvent of 2-methyltetrahydrofuran and water, and the like.

The compound (9) obtained in the step (F) can be easily isolated by a known procedure such as concentration, solvent extraction, or crystallization, and can be obtained in high purity by recrystallization.

The compound (9) obtained through the steps (A) to (F) has an excellent URAT1 inhibitory activity, and thus is useful as a agent for treating or a preventing for a disease associated with blood uric acid (e.g., hyperuricemia, gouty node, gouty arthritis, gouty kidney, urolithiasis, renal function disorder).

Incidentally, in addition to the method for producing a compound (9) comprising the steps (A) to (F) described above, the present invention also relates to the following methods (a) to (i).

(a) A method for producing a compound (9), comprising steps (B) to (F).

(b) A method for producing a compound (9), comprising steps (C) to (F).

(c) A method for producing a compound (9), comprising steps (D) to (F).

(d) A method for producing a compound (9), comprising steps (E) to (F).

(e) A method for producing a compound (3), comprising a step (A).

(f) A method for producing a compound (4), comprising a step (B).

(g) A method for producing a compound (5) or a salt thereof, comprising a step (C).

(h) A method for producing a compound (6), comprising a step (D).

(i) A method for producing a compound (8), comprising a step (E).

(j) A method for producing a compound (9), comprising, in the case where $R^2$ of a compound (8) is a group other than a methyl group, a step of converting $R^2$ into a methyl group by transesterification before a step (F).

Hereinafter, the present invention will further be specifically described with Examples below, but the present invention is not limited to those Examples.

For various reagents used in Examples, commercially available products were used otherwise noted.

For $^1$H-NMR, JNM-ECZ 400S (400 MHz) manufactured by JEOL Ltd. was used, and $^1$H-NMR was measured using tetramethylsilane as a reference.

The mass spectrum was measured by the electrospray ionization method (ESI) using ACQUITY (registered trademark) SQD manufactured by Waters Corporation.

For high-performance liquid chromatography, pump: LC-10AS, column oven: CTO-10A, and detector: SPD-10A (all manufactured by Shimadzu Corporation) were used.

Incidentally, in the case where the product was subjected to the next step without purification, part of the product, or a product separately prepared in the same manner was suitably purified, and $^1$H-NMR was then measured.

The meanings of abbreviations are shown below.
s: Singlet
d: Doublet
t: Triplet
q: Quartet
dd: Double doublet
m: Multiplet
DMSO-$d_6$: Deuterated dimethylsulfoxide
CDCl$_3$: Deuterated chloroform
CD$_3$OD: Deuterated methanol

[Example 1]: Step (A)

Synthesis of 1-(2-iodo-6-methylbenzyl)-3-methyl-6-nitro-1H-indazole [1](Hereinafter Referred to as Compound [1])

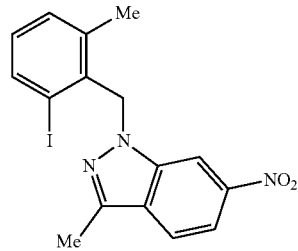 [SMILES: Cc1cccc(I)c1Cn1nc(C)c2ccc([N+](=O)[O-])cc21]

To a solution of 3-methyl-6-nitro-1H-indazole (7.74 kg, 43.9 mol) in N,N-dimethylformamide (73.6 kg, 77.5 L) was added 2-(chloromethyl)-1-iodo-3-methylbenzene (11.7 kg, 43.7 mol).

Incidentally, 3-methyl-6-nitro-1H-indazole is a compound represented by formula (1) (wherein $R^1$ represents a methyl group, and W represents a nitrogen atom).

In addition, 2-(chloromethyl)-1-iodo-3-methylbenzene is a compound represented by formula (2) (wherein L represents a methyl group, $L^2$ represents an iodine atom, and LG represents a chlorine atom).

To the obtained mixture was added potassium carbonate (7.3 kg, 52.8 mol) at 18 to 19° C. and stirred at 18 to 23° C.

for 4 hours. To the obtained mixture was further added potassium carbonate (1.8 kg, 13.0 mol) and stirred at 18 to 23° C. for 1 hour. To the obtained mixture was added water (96.3 kg) at 18 to 24° C. and stirred for 1 hour.

The resulting solid was collected by filtration and washed with water (77.0 kg). The obtained solid was dried under reduced pressure at 40° C. to give a crude material (17.1 kg). The purity of the obtained crude material was determined as an area ratio measured by high-performance liquid chromatography. The purity was 81.9% for 1-substituted compound (compound [1], compound represented by formula (3-1a)), and 15.5% for 2-substituted compound (compound represented by formula (3-1b)).

The obtained crude material was subjected to a recrystallization step. Methanol (168.4 kg, 213 L, 12.5 mL with respect to 1 g of the crude material) was added to a solution of the crude material (17.1 kg) in tetrahydrofuran (113.8 kg, 128 L, 7.5 mL with respect to 1 g of the crude material) at 55 to 61° C. over 1 hour and 10 minutes. The obtained mixture was cooled to 25° C. over 1 hour and 17 minutes, then cooled to 5° C. over 48 minutes, and further stirred at 1 to 5° C. for 1 hour.

The resulting solid was collected by filtration and washed with methanol (62 kg, 78.5 L). The obtained solid was dried under reduced pressure at 40° C. to give the title compound (compound [1]) (13.0 kg, yield: 73.0%) as a yellow solid.

The compound [1] is a compound represented by formula (3) (wherein $L^1$ represents a methyl group, $L^2$ represents iodine, $R^1$ represents a methyl group, and W represents a nitrogen atom)

The purity of the obtained compound [1] was determined as an area ratio measured by high-performance liquid chromatography. The purity of 1-substituted compound (compound [1]) was 97.6%, and 2-substituted compound was not detected.

The $^1$H-NMR data and the mass spectrum data of the compound [1] are shown below.

$^1$H-NMR (400 MHz, CDCl$_3$) δ: 8.18 (1H, d; J=1.8 Hz), 7.94 (1H, dd, J=9.2, 1.6 Hz), 7.83 (1H, d, J=7.8 Hz), 7.71 (1H, d, J=8.8 Hz), 7.21 (1H, dd, J=7.2, 1.8 Hz), 6.99 (1H, t, J=7.8 Hz), 5.73 (2H, s), 2.58 (3H, s), 2.37 (3H, s).
ESI-MS found: 408 [M+H]$^+$
High-Performance Liquid Chromatography Measurement Conditions:
Column: Inertsil ODS-3 250 mm×4.6 mm I.D., S—5 μm
Mobile phase: Acetonitrile/water/phosphoric acid=200/100/1
Flow rate: 1.0 mL/min
Detection wavelength: 220 nm

[Example 2]: Step (B)

Synthesis of 3-methyl-2-[(3-methyl-6-nitro-1H-indazol-1-yl)methyl]benzonitrile [2] (Hereinafter Referred to as Compound [2])

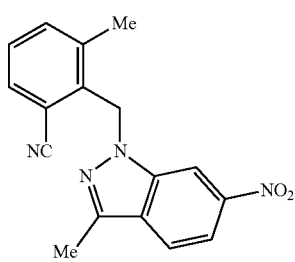 [SMILES: Cc1cccc(C#N)c1Cn1nc(C)c2ccc([N+](=O)[O-])cc21]

To a solution of the compound [1] (13.0 kg, 31.9 mol) in N,N-dimethylformamide (124 kg, 130 L) was added zinc cyanide (purity: 95%) (4.0 kg, 32.4 mol), and degassed for 1 hour. To the obtained mixture was added tetrakis(triphenylphosphine)palladium(0) (Pd(PPh$_3$)$_4$) (1.84 kg, 1.59 mol), and degassed at 14° C. for 10 minutes. The obtained mixture was stirred at 75 to 82° C. for 4 hours and then cooled to room temperature. A 23% aqueous ammonium chloride solution (130.0 kg) was added to the obtained mixture at 18 to 31° C. and further stirred at 19 to 28° C. for 1 hour.

The resulting solid was collected by filtration and washed twice with water (130 kg) and once with methanol (51 kg, 65 L) to give a crude material. Methanol (103 kg, 130 L) was added to the obtained crude material and stirred at 16 to 17° C. for 1 hour.

The solid was collected by filtration and washed with water (130 kg). The obtained solid was dried under reduced pressure at 40° C. to give the title compound (compound [2]) (9.33 kg, yield: 95.6%) as a yellow solid.

The compound [2] is a compound represented by formula (4) (wherein $L^1$ represents a methyl group, $R^1$ represents a methyl group, and W represents a nitrogen atom).

The $^1$H-NMR data and the mass spectrum data of the compound [2] are shown below.

$^1$H-NMR (400 MHz, CDCl$_3$) δ: 8.34 (1H, d, J=1.8 Hz), 7.99 (1H, dd, J=8.9, 1.6 Hz), 7.74 (1H, d, J=8.7 Hz), 7.63 (1H, d, J=7.3 Hz), 7.50-7.35 (2H, m), 5.74 (2H, s), 2.57 (3H, s), 2.35 (3H, s).
ESI-MS found: 307 [M+H]$^+$

[Example 3-1]: Step (C)

Synthesis of 2-[(6-amino-3-methyl-1H-indazol-1-yl) methyl]-3-methylbenzonitrile [3] (Hereinafter Referred to as Compound [3])

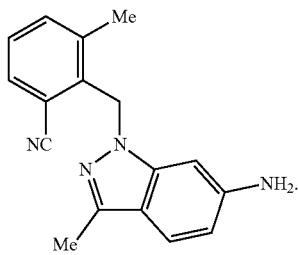 [SMILES: Cc1cccc(C#N)c1Cn1nc(C)c2ccc(N)cc21]

To a solution of the compound [2] (9.33 kg, 30.5 mol) in methanol (37 kg, 46.8 L) was added tin chloride dihydrate (27.5 kg, 122 mol). To the obtained mixture was added concentrated hydrochloric acid (44 kg, 422.4 mol) at 3 to 8° C. over 1 hour. The obtained mixture was stirred at 20 to 30° C. for 22 hours. To the obtained mixture was added 8 mol/L aqueous sodium hydroxide solution (184.7 kg) at 4 to 13° C. over 2 hours and stirred at 7 to 14° C. for 1 hour.

The resulting solid was collected by filtration and washed twice with water (47 kg). The obtained solid was dried under reduced pressure at 50° C. to give the title compound (compound [3]) (8.23 kg, yield: 97.7%) as a brown solid.

The compound [3] is a compound represented by formula (5) (wherein L represents a methyl group, $R^1$ represents a methyl group, and W represents a nitrogen atom).

The $^1$H-NMR data and the mass spectrum data of the compound [3] are shown below.

¹H-NMR (400 MHz, DMSO-d₆) δ: 7.68 (1H, d, J=7.3 Hz), 7.49 (1H, d, J=7.3H z), 7.40 (1H, t, J=7.8 Hz), 7.27 (1H, d, J=8.7 Hz), 6.48 (1H, s), 6.44 (1H, dd, J=8.7, 1.8 Hz), 5.35 (2H, s), 5.30 (2H, s), 2.22 (3H, s), 2.14 (3H, s).
ESI-MS found: 277 [M+H]⁺

[Example 3-2]: Step (C)

Synthesis of 2-[(6-amino-3-methyl-1H-indazol-1-yl)methyl]-3-methylbenzonitrile hydrochloride [4] (Hereinafter Referred to as Compound [4])

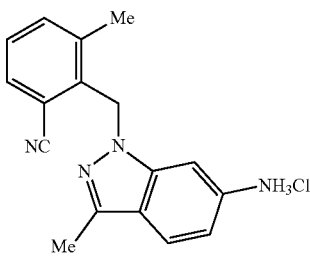

The compound [3] (8.23 kg, 29.8 mol) was added to ethyl acetate (126 kg, 140 L). To the obtained mixture was added 4 mol/L hydrogen chloride in ethyl acetate (8.77 kg, 37.3 mol) at 16 to 20° C. and stirred at 16 to 21° C. for 1 hour. The resulting solid was collected by filtration and washed with ethyl acetate (126 kg, 140 L). The obtained solid was dried under reduced pressure at 40° C. to give the title compound (compound [4]) (8.72 kg, 93.5%).

The compound [4] is a salt of a compound represented by formula (5) (wherein L¹ represents a methyl group, R¹ represents a methyl group, and W represents a nitrogen atom).

The ¹H-NMR data and the mass spectrum data of the compound [4] are shown below.

¹H-NMR (400 MHz, CD₃OD) δ: 7.86 (1H, d, J=8.2 Hz), 7.65 (1H, d, J=7.3 Hz), 7.60-7.53 (2H, m), 7.45 (1H, t, J=7.8 Hz), 7.12 (1H, d, J=8.7 Hz), 5.71 (2H, s), 2.50 (3H, s), 2.35 (3H, s).
ESI-MS found: 277 [M+H]⁺

[Example 4]: Step (D)

Synthesis of 2-[(6-iodo-3-methyl-1H-indazol-1-yl)methyl]-3-methylbenzonitrile [5] (Hereinafter Referred to as Compound [5])

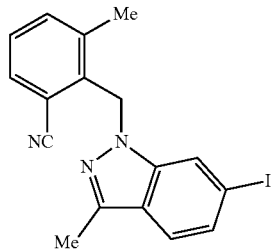 [SMILES: Cc1cccc(C#N)c1Cn1nc(C)c2ccc(I)cc21]

The compound [4] (8.72 kg, 27.9 mol) was added to acetonitrile (54 kg, 69.2 L), and concentrated hydrochloric acid (7.3 kg, 70.1 mol) was further added at -8 to -6° C. over 5 minutes. To the obtained mixture was added sodium nitrite (2.02 kg, 29.3 mol) at -6° C., and water (17 kg) was further added at -7 to 1° C. over 25 minutes. The obtained mixture was stirred at -9 to -1° C. for 1 hour.

Next, to the obtained mixture was added an acetonitrile (14 kg, 17.9 L) solution of potassium iodide (6.48 kg, 39.0 mol) at -9 to -3° C. over 30 minutes. The obtained mixture was stirred at -14 to -9° C. for 2 hours, followed by stirring at -9 to 16° C. for 16.5 hours. To the mixture was added sodium hydrogen sulfite (13.6 kg) at 16 to 18° C. To the obtained mixture were added water (87 kg) and ethyl acetate (78 kg, 86.7 L). The aqueous layer was separated and extracted with ethyl acetate (78 kg, 86.7 L). The organic layer was combined and washed with water (87 kg). The organic layer was concentrated to give a crude material.

To the obtained crude material was added acetone (69 kg, 87.3 L) and concentrated. To the obtained concentrate was added acetone (35 kg, 44.3 L) to give a mixture, then stirred at 35 to 50° C. for 1 hour. Water (87 kg) was added to the mixture at 23 to 33° C. over 14 minutes. Then, the mixture was stirred at 17 to 23° C. for 1 hour.

The resulting solid was collected by filtration and washed with water (87 kg) to give a crude material. To the obtained crude material were added methanol (55 kg, 69.6 L) and water (17 kg), and stirred at 16 to 20° C. for 1 hour. The solid was collected by filtration and washed with a mixed solution of methanol/water (methanol/water=⅔; 80 kg). The obtained solid was dried under reduced pressure at 40° C. to give the title compound (compound [5]) (7.34 kg, yield: 67.9%) as a reddish brown solid.

The compound [5] is a compound represented by formula (6) (wherein L¹ represents a methyl group, R¹ represents a methyl group, W represents a nitrogen atom, and $X_L$ represents an iodine atom).

The ¹H-NMR data and the mass spectrum data of the compound [5] are shown below.

¹H-NMR (400 MHz, CDCl₃) δ: 7.73 (1H, s), 7.60 (1H, d, J=6.4 Hz), 7.48-7.34 (4H, m), 5.63 (2H, s), 2.51 (3H, s), 2.29 (3H, s).
ESI-MS found: 388 [M+H]⁺

[Example 5]: Step (E)

Synthesis of methyl [1-(2-cyano-6-methylbenzyl)-3-methyl-1H-indazol-6-yl]difluoroacetate [6] (Hereinafter Referred to as Compound [6])

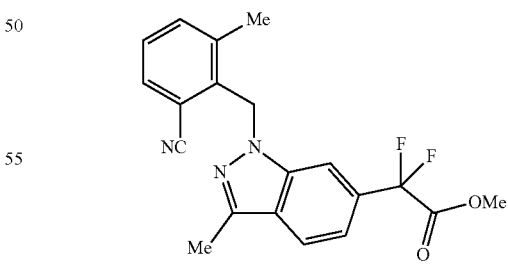

Tetrahydrofuran (84.6 kg, 95.0 L), the compound [5] (25.0 kg, 64.6 mol), and copper (powder) (36.9 kg, 581 mol) were added to dimethyl sulfoxide (311 kg, 282.7 L). To the obtained mixture was added methyl bromodifluoroacetate (compound represented by formula (7) (wherein R² represents a methyl group, and R³ represents a bromine atom) (30.5 kg, 161 mol) at 18° C. over 5 minutes. The obtained mixture was stirred at 30 to 36° C. for 6 hours. Next, to the mixture was added ethyl acetate (450 kg, 500 L), followed by a 10% aqueous solution of potassium dihydrogen phosphate (500 kg) at 19 to 27° C. over 35 minutes. The obtained mixture was stirred at 17 to 20° C. for 1 hour.

Insolubles were filtered and washed three times with ethyl acetate (180 kg, 200 L). The organic layer was separated and washed twice with a 25% aqueous sodium chloride solution (332.5 kg). Ethyl acetate (22.5 kg, 25 L), magnesium sulfate (25.0 kg), and activated carbon (2.50 kg) were added to the organic layer and stirred at 19 to 24° C. for 30 minutes.

Insolubles were collected by filtration and washed with ethyl acetate (225 kg, 250 L). The filtrate was concentrated under reduced pressure, then methanol (59.3 kg, 75 L) was added, and the mixture was concentrated again under reduced pressure to give a crude material.

To the obtained crude material was added methanol (59.3 kg, 75 L) to give a mixture, and stirred at 62 to 65° C. for 1 hour. The mixture was cooled to 20° C. over 1 hour and 17 minutes. Next, the mixture was cooled to 5° C. over 33 minutes. The mixture was further stirred at −2 to 5° C. for 1.5 hours.

The obtained solid was filtered and washed with methanol cooled to −2° C. (25.7 kg, 32.5 L). The obtained solid was dried under reduced pressure to give the title compound (compound [6]) (17.4 kg, yield: 72.9%) as a white solid.

The compound [6] is a compound represented by formula (8) (wherein $L^1$ represents a methyl group, $R^1$ represents a methyl group, $R^2$ represents a methyl group, and W represents a nitrogen atom).

The $^1$H-NMR data and the mass spectrum data of the compound [6] are shown below.

$^1$H-NMR (400 MHz, CDCl$_3$) δ: 7.71 (1H, dd, J=8.4, 0.8 Hz), 7.66-7.59 (2H, m), 7.43 (1H, d, J=6.9 Hz), 7.40-7.32 (2H, m), 5.70 (2H, s), 3.84 (3H, s), 2.54 (3H, s), 2.31 (3H, s).

ESI-MS found: 370 [M+H]$^+$

[Example 6]: Step (F)

Synthesis of [1-(2-cyano-6-methylbenzyl)-3-methyl-1H-indazol-6-yl]difluoroacetic acid [7] (Hereinafter Referred to as Compound [7])

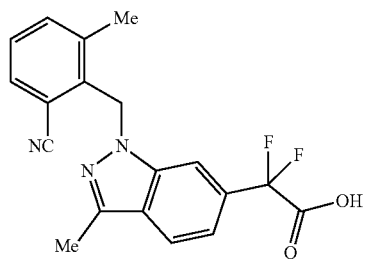 [SMILES: Cc1cccc(C#N)c1Cn1nc(C)c2ccc(C(F)(F)C(=O)O)cc21]

To a solution of the compound [6] (12.4 kg, 33.6 mol) in tetrahydrofuran (55.2 kg, 62 L) was added 1 mol/L aqueous sodium hydroxide solution (64.5 kg, 62.0 mol) at 15 to 21° C. over 40 minutes. The obtained mixture was stirred at 18 to 21° C. for 30 minutes.

Water (124 kg) and diisopropyl ether (86.8 kg, 124 L) were added to the mixture and stirred for 10 minutes. The aqueous layer was separated, and ethyl acetate (167 kg, 185.6 L) was added. 1 mol/L hydrochloric acid (80.3 kg) was added to the obtained mixture at 17 to 19° C. over 23 minutes.

The organic layer was separated and washed twice with a 5% aqueous sodium chloride solution (130.6 kg). Ethyl acetate (11.2 kg, 12.4 L), magnesium sulfate (12.4 kg), and activated carbon (1.24 kg) were added to the organic layer and stirred at 18 to 21° C. for 30 minutes.

Insolubles were filtered and washed with ethyl acetate (167 kg, 185.6 L). The filtrate was concentrated to give a crude material.

To the obtained crude material was added acetone (24.5 kg, 31 L), and stirred at 50 to 56° C. for 35 minutes. The obtained mixture was cooled to 20° C. over 2 hours, and then water (186 kg) was added at 18 to 22° C. over 45 minutes. The obtained mixture was cooled to 5° C. over 45 minutes and stirred at 0 to 5° C. for 1 hour.

The obtained solid was collected by filtration, and washed with an mixed solvent of acetone/water cooled to 3° C. (2.9 kg of acetone/22.3 kg of water) and water (62.0 kg). The obtained solid was dried under reduced pressure at 80° C. to give the title compound (compound [7]) (10.8 kg, yield: 91%) as white crystals.

The compound [7] is a compound represented by formula (9) (wherein $L^1$ represents a methyl group, $R^1$ represents a methyl group, and W represents a nitrogen atom).

The $^1$H-NMR data and the mass spectrum data of the compound [7] are shown below.

$^1$H-NMR (400 MHz, CD$_3$OD) δ: 7.74 (1H, s), 7.71 (1H, d, J=8.5 Hz), 7.55 (1H, d, J=7.6 Hz), 7.40 (1H, d, J=7.3 Hz), 7.32 (1H, t, J=7.7 Hz), 7.25 (1H, d, J=8.5 Hz), 5.65 (2H, s), 2.40 (3H, s), 2.13 (3H, s).

ESI-MS found: 356[M+H]$^+$

In the above Examples 1 to 6 (step (A) to step (F)), it was possible to produce a difluoromethylene compound on the order of kilograms without using column chromatography.

In addition, although Patent Literature 1 requires two steps (Schemes 6 and 7) in order to introduce two fluorine atoms (difluoroacetic acid group), in Example 5 (Step (E)) of the present application, it was possible to introduce two fluorine atoms (difluoroacetic acid group) in one step.

Further, in step (2) of Example 24 of Patent Literature 1 (corresponding to Scheme 7 of Patent Literature 1), a reaction at a low temperature (−78° C.) and column chromatography are used, and also the yield was 48%. Meanwhile, in Example 5 (Step (E)) of the present application, it was possible to efficiently introduce two fluorine atoms without using the low temperature or column chromatography, and also the yield was 72.9%.

These results show that the present invention is applicable to the industrial production of difluoromethylene compounds.

[Example 7]: Step (E)

Synthesis of Ethyl [1-(2-cyano-6-methylbenzyl)-3-methyl-1H-indazol-6-yl]difluoroacetate [8] (Hereinafter Referred to as Compound [8])

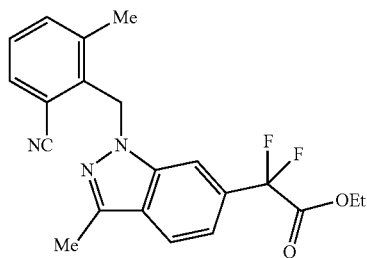 [SMILES: CCOC(=O)C(F)(F)c1ccc2c(C)nn(Cc3c(C)cccc3C#N)c2c1]

Tetrahydrofuran (24.8 kg, 27.9 L), the compound [5] (7.34 kg, 19.0 mol), and copper (powder) (10.8 kg, 170 mol) were added to dimethyl sulfoxide (91.2 kg, 82.9 L). To the obtained mixture was added ethyl bromodifluoroacetate (compound represented by formula (7) (wherein $R^2$ represents an ethyl group, and $R^3$ represents a bromine atom) (9.62 kg, 47.4 mol) at 15 to 16° C. over 5 minutes. The obtained mixture was stirred at 30 to 35° C. for 7 hours. Then, to the mixture were added ethyl acetate (132 kg, 146.7 L), and a 10% aqueous solution of potassium dihydrogen phosphate (146.7 kg) over 37 minutes. The obtained mixture was stirred at 18 to 26° C. for 1 hour.

Insolubles were filtered, then washed twice with ethyl acetate (66.1 kg, 73.4 L), and further washed with ethyl acetate (33.0 kg, 36.7 L). Water (73.4 kg) was added to the filtrate and stirred for 10 minutes. The organic layer was separated and washed twice with a 25% aqueous sodium chloride solution (97.6 kg). Ethyl acetate (6.61 kg, 7.34 L), magnesium sulfate (7.34 kg), and activated carbon (0.73 kg) were added to the organic layer and stirred at 20 to 21° C. for 30 minutes.

Insolubles were filtered and washed with ethyl acetate (66.1 kg, 73.4 L). The filtrate was concentrated under reduced pressure, then methanol (17.4 kg, 22 L) was added, and the mixture was concentrated under reduced pressure again to give the title compound as an oil.

The product (compound [8]) was used in the next step (Example 8) without further purification.

The compound [8] is a compound represented by formula (8) (wherein L represents a methyl group, $R^1$ represents a methyl group, $R^2$ represents an ethyl group, and W represents a nitrogen atom).

The $^1$H-NMR data and the mass spectrum data of the compound [8] are shown below.

$^1$H-NMR (400 MHz, CDCl$_3$) δ: 7.71 (1H, dd, J=8.4, 0.8 Hz), 7.66-7.59 (2H, m), 7.43 (1H, d, J=6.9 Hz), 7.40-7.32 (2H, m), 5.71 (2H, s), 4.30 (2H, q, J=7.1 Hz), 2.54 (3H, s), 2.30 (3H, s), 1.29 (3H, t, J=7.1 Hz).

ESI-MS found: 384[M+H]$^+$

[Example 8]: Step (E-1)

Synthesis of Methyl [1-(2-cyano-6-methylbenzyl)-3-methyl-1H-indazol-6-yl]difluoroacetate (Compound [6])

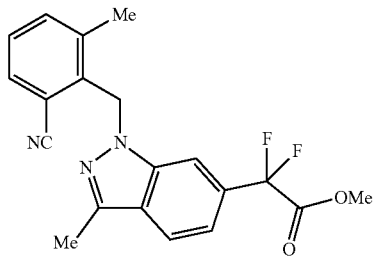 [SMILES: COC(=O)C(F)(F)c1ccc2c(C)nn(Cc3c(C)cccc3C#N)c2c1]

Methanol (17.4 kg, 22 L) and concentrated sulfuric acid (0.38 kg, 3.8 mol) were added to the compound [8] obtained in Example 7 (19.0 mol (based on the compound [5] used in Example 7)). The obtained mixture was stirred at 55 to 63° C. for 5 hours. Next, the mixture was cooled to 20° C. over 1 hour and 10 minutes, cooled to 5° C. over 35 minutes, and then subsequently stirred at −3 to 5° C. for 1.5 hours.

The resulting solid was collected by filtration and washed with methanol cooled to −5° C. (11.6 kg, 14.7 L). The obtained solid was dried under reduced pressure to give the title compound (compound [6]) (4.00 kg, the overall yield from the compound [5] used in Example 7: 57%) as a white solid.

[Example 9]: Step (B)

Synthesis of 3-methyl-2-[(3-methyl-6-nitro-1H-indazol-1-yl)methyl]benzonitrile (Compound [2])

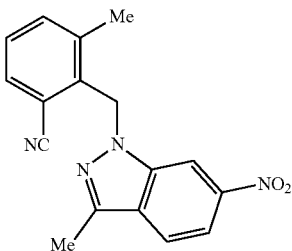 [SMILES: Cc1cccc(C#N)c1Cn1nc(C)c2ccc([N+](=O)[O-])cc21]

To a solution of the compound [1] (1.00 g, 2.46 mmol) in N,N-dimethylformamide (10 mL) were added L-proline (0.28 g, 2.43 mmol) and copper cyanide (0.44 g, 4.91 mmol) and stirred at 115 to 118° C. for 3 hours. The obtained mixture was cooled to room temperature, and a saturated aqueous solution of ammonium chloride (10 mL) was added at 20 to 30° C. To the obtained mixture was added ethyl acetate (20 mL) at 30° C. and stirred at 30° C. for 30 minutes. Insolubles were filtered and washed three times with ethyl acetate (10 mL). The filtrate was combined and washed twice with a saturated aqueous solution of sodium chloride (20 mL). Magnesium sulfate (1.00 g) and activated carbon (0.10 g) were added to the organic layer. Insolubles were filtered, and the filtrate was concentrated under reduced pressure to give a brown solid.

Methanol (10 mL) was added to the obtained brown solid and stirred at 20° C. for 1 hour.

The resulting solid was collected by filtration and dried under reduced pressure at 40° C. to give the title compound (compound [2]) (0.69 g, yield: 92%) as a yellow solid.

The following Reference Examples 1 to 3 show a synthesis example of 2-(chloromethyl)-1-iodo-3-methylbenzene (compound represented by formula (2) (wherein $L^1$ represents a methyl group, $L^2$ represents iodine, and LG represents a chlorine atom)) used in Example 1.

Reference Example 1

Synthesis of (2-amino-6-methylphenyl)methanol (Hereinafter Referred to as Compound [A-1])

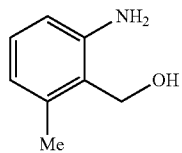

To a mixed solution of a 70% toluene solution of sodium bis (2-methoxyethoxy) aluminum hydride (315 kg) and toluene (86.1 kg), was added a tetrahydrofuran (147 kg) solution of 2-amino-6-methylbenzoic acid (33.0 kg) at 35 to 40° C. over 3 hours. The obtained mixture was stirred at 37° C. for 30 minutes and then cooled to 10° C. Next, the mixture was added to an aqueous (660 kg) solution of potassium sodium tartrate tetrahydrate (425 kg) at 1 to 21° C. over 1 hour. The aqueous layer was separated and extracted twice with toluene (144 kg). The organic layer was combined, and magnesium sulfate (39.6 kg) was added. Insolubles were collected by filtration and washed with toluene (144 kg). The filtrate was concentrated to 100 L, and heptane (273 kg) was added at 56 to 60° C. over 1 hour and 45 minutes. The obtained mixture was cooled to 5° C. over 1.5 hours and then stirred for 1 hour. The resulting solid was collected by filtration and washed with a heptane/toluene mixed solvent cooled to −3° C. (heptane (45.5 kg)/toluene (14.4 kg)). The obtained solid was dried under reduced pressure at 40° C. to give the title compound (compound [A-1]) (24.9 kg, yield: 83%) as a white solid.

Reference Example 2

Synthesis of (2-iodo-6-methylphenyl)methanol (Hereinafter Referred to as Compound [A-2])

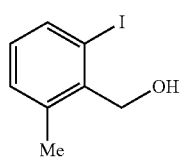

Water (24.9 kg) and ethyl acetate (112 kg) were added to the compound [A-1] (24.9 kg). To the obtained mixture was added dilute sulfuric acid (sulfuric acid (90.6 kg)/water (99.6 kg)) at 1 to 14° C. over 50 minutes. An aqueous sodium nitrite solution (sodium nitrite (13.8 kg)/water (24.9 kg)) was added to the obtained mixture at −3 to 3° C. over 55 minutes. The obtained mixture was stirred at −3 to 3° C. for 30 minutes. Next, the mixture was added to a mixed solvent of water (125 kg)/potassium iodide (60.3 kg)/ethyl acetate (112 kg) at −3 to 10° C. over 30 minutes. The obtained mixture was stirred at 10 to 14° C. for 30 minutes. Ethyl acetate (112 kg) was added to the mixture to separate the organic layer. The organic layer was washed with an aqueous (125 kg) solution of sodium thiosulfate pentahydrate (135 kg) and a 20% aqueous solution of sodium chloride (sodium chloride (24.9 kg)/water (99.6 kg)). The separated organic layer was filtered and washed with ethyl acetate (67.2 kg). Water (249 kg) was added to the filtrate and concentrated to about 270 L. The obtained mixture was stirred at 20 to 25° C. for 30 minutes. The resulting solid was collected by filtration and washed with water (498 kg). The obtained solid was dried under reduced pressure at 40° C. to give the title compound ([A-2]) (41.4 kg, yield: 92%) as a yellow solid.

Reference Example 3

Synthesis of 2-(chloromethyl)-1-iodo-3-methylbenzene (Hereinafter Referred to as Compound [A-3])

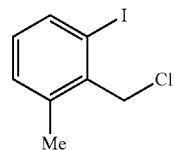

To a solution of the compound [A-2] (41.4 kg) in N,N-dimethylformamide (197 kg) was added thionyl chloride (39.7 kg) at 1 to 11° C. over 1 hour and 10 minutes. The obtained mixture was stirred at 15 to 24° C. for 1 hour. Next, water (207 kg) was added to the mixture at 1 to 26° C. over 1 hour and then stirred for 1 hour. The resulting solid was collected by filtration, and washed with water (414 kg) and a mixed solvent of methanol/water (methanol (81.8 kg)/water (104 kg)). The obtained solid was dried under reduced pressure at 25° C. to give the title compound (compound [A-3]) (41.4 kg, yield: 93%) as a yellow solid.

The $^1$H-NMR data of the compound [A-3] are shown below.

$^1$H-NMR (400 MHz, CDCl$_3$) δ: 7.73 (1H, d, J=8.1 Hz), 7.16 (1H, d, J=7.3 Hz), 6.90 (1H, t, J=7.8 Hz), 4.81 (2H, s), 2.52 (3H, s).

Hereinafter, Example 10 regarding the step (D) will be shown. In Example 10, the compound [3] obtained in Example 3-1 was not converted into a compound [4], which is a hydrochloride thereof, but directly subjected to the step (D) to obtain the compound [5].

[Example 10]: Step (D)

Synthesis of 2-[(6-iodo-3-methyl-1H-indazol-1-yl)methyl]-3-methylbenzonitrile [5] (Hereinafter Referred to as Compound [5])

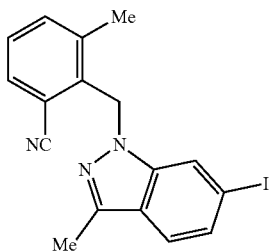 [SMILES: Cc1cccc(C#N)c1Cn1nc(C)c2ccc(I)cc21]

The compound [3] (5.00 g, 18.1 mmol) was added to acetonitrile (40 mL), and concentrated hydrochloric acid (4.70 g, 45.3 mmol) was further added at −10 to −5° C. over 4 minutes. Acetonitrile (5 mL) and water (25 mL) were added to the obtained mixture. To the obtained mixture was added an aqueous (7.5 mL) solution of sodium nitrite (1.30 g, 19.0 mmol) at −7 to −2° C., and further added water (2.5 mL). The obtained mixture was stirred at −5 to −2° C. for 30 minutes.

The mixture obtained above was added to a suspension of potassium iodide (4.20 g, 25.3 mmol) in acetonitrile (5.0 mL) at −9 to −2° C. over 19 minutes, and water (2.5 mL) was further added. The obtained mixture was stirred at −9 to −7° C. for 30 minutes. Sodium hydrogen sulfite (8.85 g) was added to the mixture at −8 to −7° C. Water (50 mL) and ethyl acetate (50 mL) were added to the obtained mixture. The aqueous layer was separated and extracted with ethyl acetate (50 mL). The organic layer was combined and washed with water (50 mL). The organic layer was concentrated to give a crude material.

Tetrahydrofuran (5.0 mL) and methanol (20 mL) were added to the obtained crude material and stirred at 60 to 61° C. for 20 minutes. Water (7.5 mL) was added to the obtained mixture over 3 minutes, stirred at 58 to 61° C. for 1 hour, and then stirred at 19 to 25° C. for 1 hour.

The resulting solid was collected by filtration and washed with a methanol/water mixed solution (methanol/water=8/3; 20 mL). The obtained solid was dried under reduced pressure at 40° C. to give the title compound (compound [5]) (5.94 g, yield: 84.7%) as a brown solid.

INDUSTRIAL APPLICABILITY

The present invention is applicable in the pharmaceutical field.

The invention claimed is:

1. A method for producing a compound represented by formula (9):

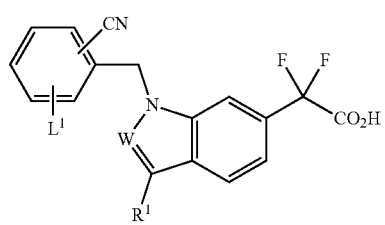

[wherein
- $L^1$ represents a halogen atom, a cyano group, a lower alkyl group, a halo-lower alkyl group, a cycloalkyl group, a lower alkoxy group, a halo-lower alkoxy group, or a hydroxy lower alkyl group;
- $R^1$ represents a lower alkyl group, a halogen atom, a halo-lower alkyl group, a cycloalkyl group, a cyano group, or a hydroxy lower alkyl group; and
- W represents a nitrogen atom or a methine group], the method comprising the following steps (A) to (F):

a step (A): a step of allowing a compound represented by formula (1):

[wherein $R^1$, and W are as defined above]
to react with a compound represented by formula (2):

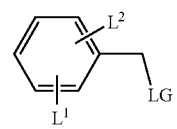

[wherein
- $L^1$ is as defined above;
- $L^2$ is a halogen atom or a group represented by $-OSO_2R^4$;
- $R^4$ represents a lower alkyl group, a halo-lower alkyl group, or an aryl group (wherein the aryl group is optionally substituted with a halogen atom, a lower alkyl group, or a lower alkoxy group);
- LG is a halogen atom or a group represented by $-OSO_2R^5$; and
- $R^5$ represents a lower alkyl group, a halo-lower alkyl group, or an aryl group (wherein the aryl group is optionally substituted with a halogen atom, a lower alkyl group, or a lower alkoxy group)]

to give a compound represented by formula (3):

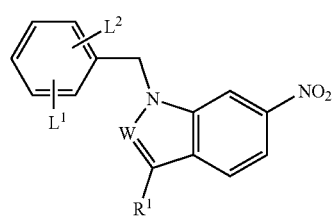

[wherein $L^1$, $L^2$, $R^1$, and W are as defined above], a step (B): a step of cyanating $L^2$ of the compound represented by formula (3) to give a compound represented by formula (4):

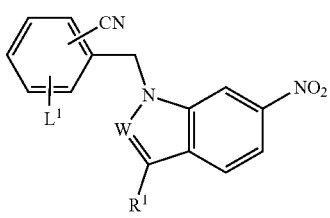

(4)

[wherein $L^1$, $R^1$, and W are as defined above], a step (C): a step of reducing a nitro group of the compound represented by formula (4) to give a compound represented by formula (5):

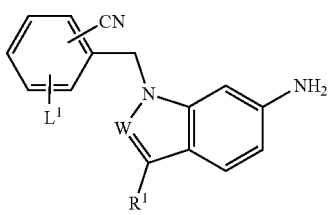

(5)

[wherein $L^1$, $R^1$, and W are as defined above] or a salt thereof, a step (D): a step of halogenating an amino group of the compound represented by formula (5) or salt thereof to give a compound represented by formula (6):

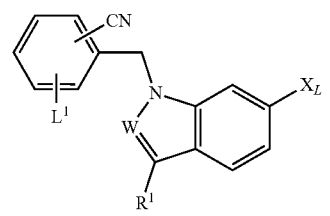

(6)

[wherein $L^1$, $R^1$, and W are as defined above, and $X_L$ is a halogen atom], a step (E): a step of allowing the compound represented by formula (6) to react with a compound represented by formula (7):

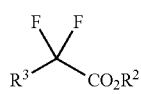

(7)

[wherein $R^2$ represents a lower alkyl group, a halo-lower alkyl group, a cycloalkyl group, a lower alkenyl group, or an aralkyl group; and $R^3$ represents a chlorine atom, a bromine atom, or an iodine atom] to give a compound represented by formula (8):

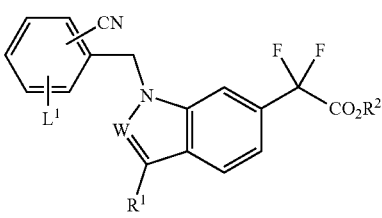

(8)

[wherein $L^1$, $R^1$, $R^2$, and W are as defined above], and a step (F): a step of removing $R^2$ of the compound represented by formula (8).

2. A method for producing a compound represented by formula (9):

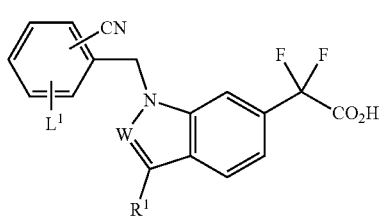

(9)

[wherein $L^1$ represents a halogen atom, a cyano group, a lower alkyl group, a halo-lower alkyl group, a cycloalkyl group, a lower alkoxy group, a halo-lower alkoxy group, or a hydroxy lower alkyl group;

$R^1$ represents a lower alkyl group, a halogen atom, a halo-lower alkyl group, a cycloalkyl group, a cyano group, or a hydroxy lower alkyl group; and W represents a nitrogen atom or a methine group], the method comprising the following steps (B) to (F):

a step (B): a step of cyanating $L^2$ of a compound represented by formula (3):

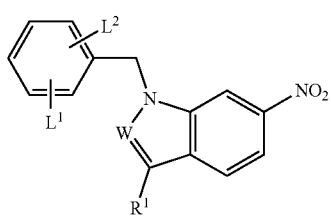

(3)

[wherein $L^1$, $R^1$, and W are as defined above;

$L^2$ is a halogen atom or a group represented by $-OSO_2R^4$; and $R^4$ represents a lower alkyl group, a halo-lower alkyl group, or an aryl group (wherein the aryl group is optionally substituted with a halogen atom, a lower alkyl group, or a lower alkoxy group)]

to give a compound represented by formula (4):

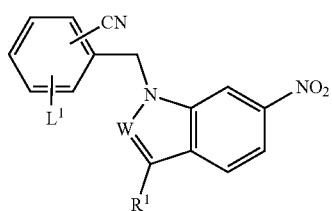
(4)

[wherein $L^1$, $R^1$, and W are as defined above],
a step (C): a step of reducing a nitro group of the compound represented by formula (4) to give a compound represented by formula (5):

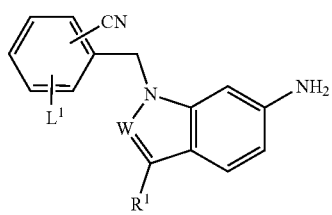
(5)

[wherein $L^1$, $R^1$, and W are as defined above]
or a salt thereof,
a step (D): a step of halogenating an amino group of the compound represented by formula (5) or salt thereof to give a compound represented by formula (6):

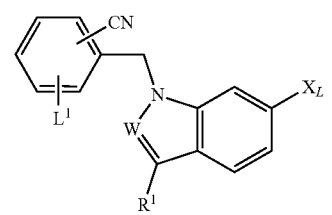
(6)

[wherein $L^1$, $R^1$, and W are as defined above, and $X_L$ is a halogen atom],
a step (E): a step of allowing the compound represented by formula (6) to react with a compound represented by formula (7):

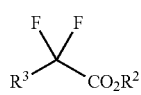
(7)

[wherein
$R^2$ represents a lower alkyl group, a halo-lower alkyl group, a cycloalkyl group, a lower alkenyl group, or an aralkyl group; and
$R^3$ represents a chlorine atom, a bromine atom, or an iodine atom]

to give a compound represented by formula (8):

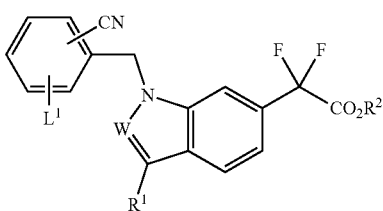
(8)

[wherein $L^1$, $R^1$, $R^2$, and W are as defined above], and
a step (F): a step of removing $R^2$ of the compound represented by formula (8).

3. A method for producing a compound represented by formula (9):

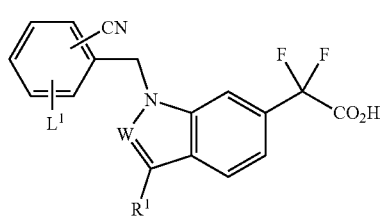
(9)

[wherein
$L^1$ represents a halogen atom, a cyano group, a lower alkyl group, a halo-lower alkyl group, a cycloalkyl group, a lower alkoxy group, a halo-lower alkoxy group, or a hydroxy lower alkyl group;
$R^1$ represents a lower alkyl group, a halogen atom, a halo-lower alkyl group, a cycloalkyl group, a cyano group, or a hydroxy lower alkyl group; and
W represents a nitrogen atom or a methine group],
the method comprising the following steps (C) to (F):
a step (C): a step of reducing a nitro group of a compound represented by formula (4):

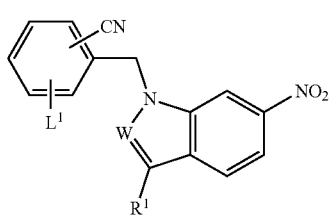
(4)

[wherein $L^1$, $R^1$, and W are as defined above]
to give a compound represented by formula (5):

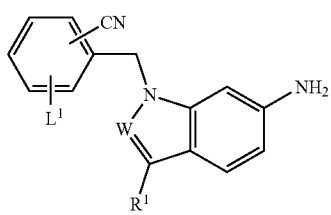
(5)

[wherein $L^1$, $R^1$, and W are as defined above]

or a salt thereof,
a step (D): a step of halogenating an amino group of the compound represented by formula (5) or salt thereof to give a compound represented by formula (6):

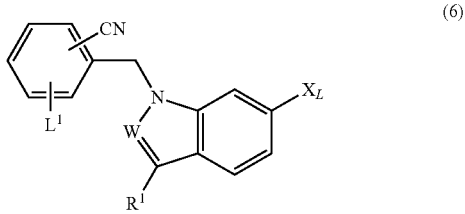

(6)

[wherein $L^1$, $R^1$, and W are as defined above, and $X_L$ is a halogen atom],
a step (E): a step of allowing the compound represented by formula (6) to react with a compound represented by formula (7):

(7)

[wherein
$R^2$ represents a lower alkyl group, a halo-lower alkyl group, a cycloalkyl group, a lower alkenyl group, or an aralkyl group; and
$R^3$ represents a chlorine atom, a bromine atom, or an iodine atom] to give a compound represented by formula (8):

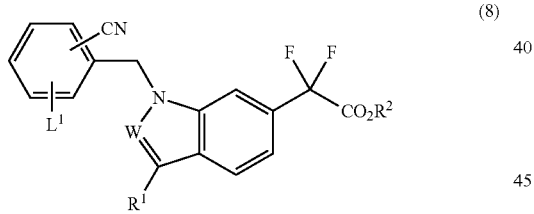

(8)

[wherein $L^1$, $R^1$, $R^2$, and W are as defined above], and
a step (F): a step of removing $R^2$ of the compound represented by formula (8).

4. A method for producing a compound represented by formula (9):

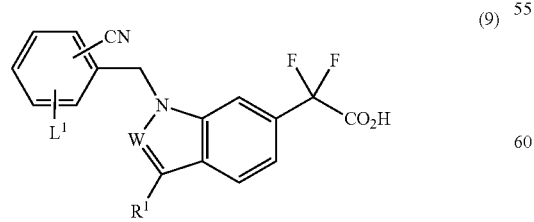

(9)

[wherein
$L^1$ represents a halogen atom, a cyano group, a lower alkyl group, a halo-lower alkyl group, a cycloalkyl group, a lower alkoxy group, a halo-lower alkoxy group, or a hydroxy lower alkyl group;
$R^1$ represents a lower alkyl group, a halogen atom, a halo-lower alkyl group, a cycloalkyl group, a cyano group, or a hydroxy lower alkyl group; and
W represents a nitrogen atom or a methine group],
the method comprising the following steps (D) to (F):
a step (D): a step of halogenating an amino group of a compound represented by formula (5):

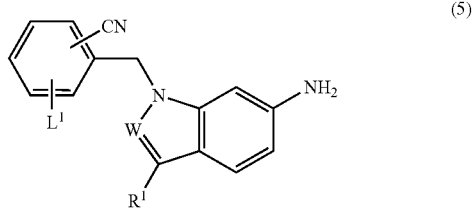

(5)

[wherein $L^1$, $R^1$, and W are as defined above]
or a salt thereof to give a compound represented by formula (6):

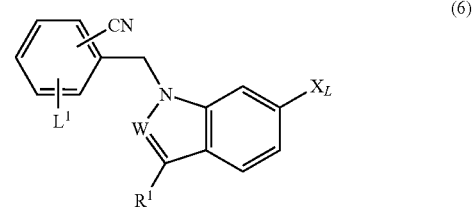

(6)

[wherein $L^1$, $R^1$, and W are as defined above, and $X_L$ is a halogen atom],
a step (E): a step of allowing the compound represented by formula (6) to react with a compound represented by formula (7):

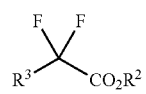

(7)

[wherein
$R^2$ represents a lower alkyl group, a halo-lower alkyl group, a cycloalkyl group, a lower alkenyl group, or an aralkyl group; and
$R^3$ represents a chlorine atom, a bromine atom, or an iodine atom] to give a compound represented by formula (8):

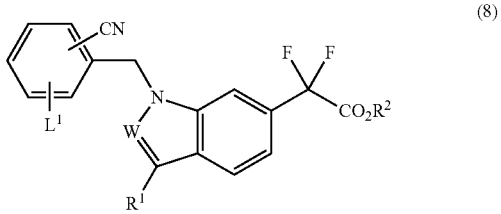

(8)

[wherein L¹, R¹, R², and W are as defined above], and a step (F): a step of removing R² of the compound represented by formula (8).

5. A method for producing a compound represented by formula (9):

(9)

[wherein
L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group; and W represents a nitrogen atom or a methine group], the method comprising the following steps (E) to (F):

a step (E): a step of allowing a compound represented by formula (6):

(6)

[wherein
L¹, R¹, and W are as defined above; and $X_L$ represents a halogen atom]

to react with a compound represented by formula (7):

(7)

[wherein
R² represents a lower alkyl group, a halo-lower alkyl group, a cycloalkyl group, a lower alkenyl group, or an aralkyl group; and R³ represents a chlorine atom, a bromine atom, or an iodine atom]

to give a compound represented by formula (8):

(8)

[wherein L¹, R¹, R², and W are as defined above], and a step (F): a step of removing R² of the compound represented by formula (8).

6. A method for producing a compound represented by formula (8):

(8)

[wherein
L¹ represents a halogen atom, a cyano group, a lower alkyl group, a halo-lower alkyl group, a cycloalkyl group, a lower alkoxy group, a halo-lower alkoxy group, or a hydroxy lower alkyl group;

R¹ represents a lower alkyl group, a halogen atom, a halo-lower alkyl group, a cycloalkyl group, a cyano group, or a hydroxy lower alkyl group;

R² represents a lower alkyl group, a halo-lower alkyl group, a cycloalkyl group, a lower alkenyl group, or an aralkyl group; and W represents a nitrogen atom or a methine group], the method comprising the following step (E): a step of allowing a compound represented by formula (6):

(6)

[wherein
L¹, R¹, and W are as defined above; and $X_L$ is a halogen atom]

to react with a compound represented by formula (7):

(7)

[wherein
R² is as defined above; and
R³ represents a chlorine atom, a bromine atom, or an iodine atom].

7. The method according to any one of claims 1 to 5 and 6, wherein R¹ is a lower alkyl group, and/or; wherein L¹ is a lower alkyl group; and/or wherein W is a nitrogen atom.

8. The method according to claim 1, wherein a base used in the step (A) is potassium carbonate or cesium carbonate.

9. The method according to claim 1, further comprising a step (A-2): a step of recrystallizing the compound represented by formula (3) using a recrystallization solvent that is a combination of tetrahydrofuran and methanol.

10. The method according to claim 1 or 2, wherein a cyanating agent used in the step (B) is zinc cyanide, and/or wherein in the step (B), a palladium catalyst or a combination of a palladium catalyst and a phosphine ligand is used.

11. The method according to claim 1 or 2, wherein a cyanating agent used in the step (B) is copper cyanide.

12. The method according to any one of claims 1 to 5 and 6, wherein R² of the compound represented by formula (7) is a lower alkyl group.

13. The method according to claim 12, wherein the compound represented by formula (7) is methyl bromodifluoroacetate or ethyl bromodifluoroacetate.

14. The method according to any one of claims 1 to 5 and 6, wherein a reaction solvent in the step (E) is dimethyl sulfoxide or a mixed solvent of dimethyl sulfoxide and tetrahydrofuran.

15. The method according to any one of claims 1 to 5, comprising, in the case where R² of the compound represented by formula (8) is a group other than a methyl group, a step of transesterifying the R² into a methyl group before the step (F).

16. A compound of the following (a) to (g):
(a) 1-(2-iodo-6-methylbenzyl)-3-methyl-6-nitro-1H-indazole;
(b) 3-methyl-2-[(3-methyl-6-nitro-1H-indazol-1-yl)methyl]benzonitrile;
(c) 2-[(6-amino-3-methyl-1H-indazol-1-yl)methyl]-3-methylbenzonitrile;
(d) 2-[(6-amino-3-methyl-1H-indazol-1-yl)methyl]-3-methylbenzonitrile hydrochloride;
(e) 2-[(6-iodo-3-methyl-1H-indazol-1-yl)methyl]-3-methylbenzonitrile;
(f) Methyl [1-(2-cyano-6-methylbenzyl)-3-methyl-1H-indazol-6-yl]difluoroacetate; or
(g) Ethyl [1-(2-cyano-6-methylbenzyl)-3-methyl-1H-indazol-6-yl]difluoroacetate.

\* \* \* \* \*